Figure 1:
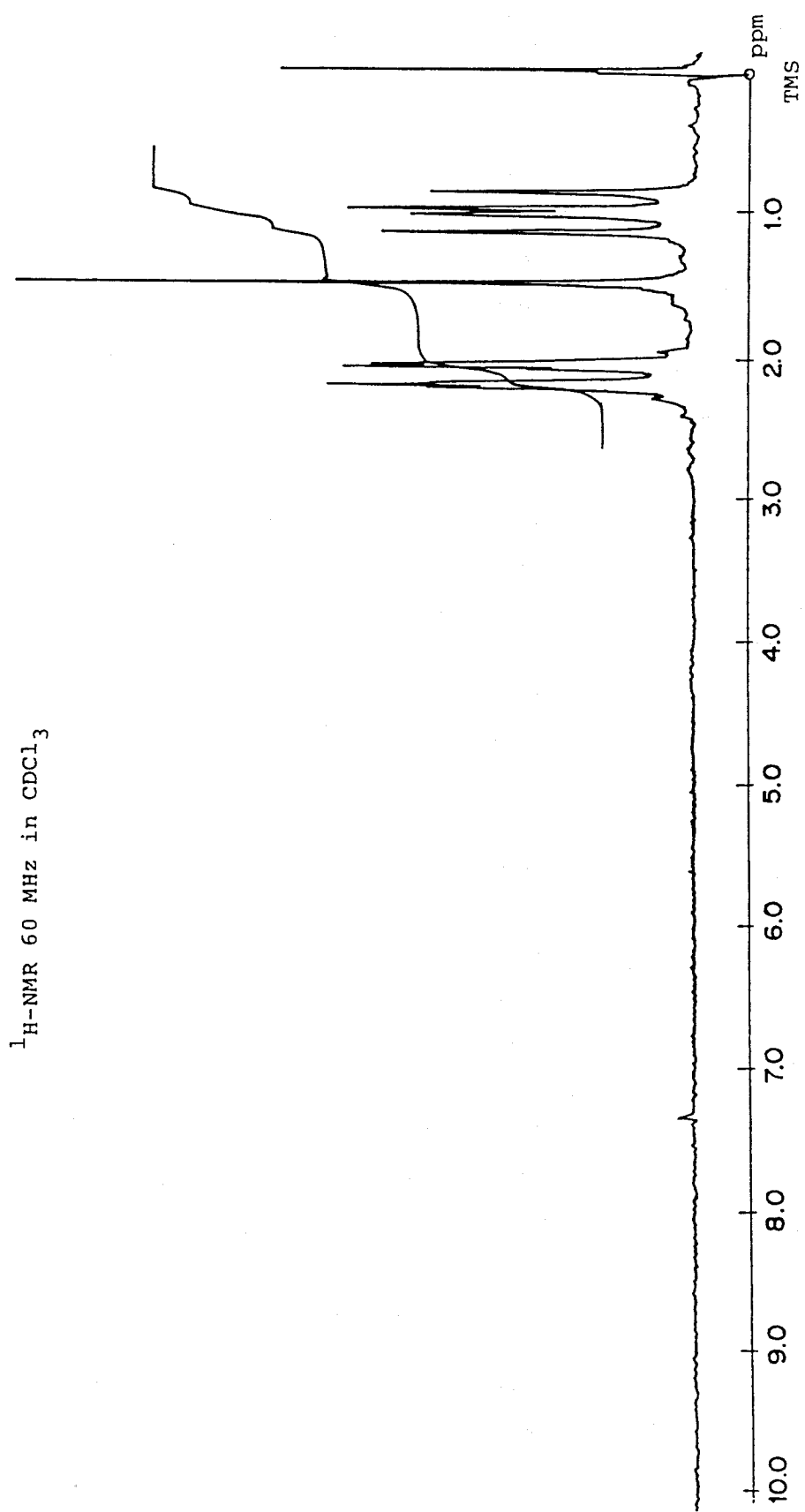

United States Patent [19]

Kohsaka et al.

[11] Patent Number: 5,059,237
[45] Date of Patent: Oct. 22, 1991

[54] BUTENOIC ACID DERIVATIVES AND USE AS HERBICIDES

[75] Inventors: Hideo Kohsaka; Masayuki Takase, both of Takarazuka, Japan

[73] Assignee: Sumitomo Chemical Company, Limited, Osaka, Japan

[21] Appl. No.: 895,998

[22] Filed: Aug. 13, 1986

[30] Foreign Application Priority Data

| Aug. 13, 1985 | [JP] | Japan | 60-177978 |
| Aug. 13, 1985 | [JP] | Japan | 60-177979 |
| Oct. 15, 1985 | [JP] | Japan | 60-230536 |
| Feb. 20, 1986 | [JP] | Japan | 61-35570 |
| Mar. 10, 1986 | [JP] | Japan | 61-52304 |
| May 20, 1986 | [JP] | Japan | 61-115905 |
| May 28, 1986 | [JP] | Japan | 61-122924 |
| Jun. 11, 1986 | [JP] | Japan | 61-135595 |
| Jun. 17, 1986 | [JP] | Japan | 61-142275 |

[51] Int. Cl.$^5$ .................. A01N 43/48; C07D 233/00; C07D 235/00
[52] U.S. Cl. ........................ 71/92; 548/301; 548/302; 548/101; 548/108
[58] Field of Search .............. 548/301, 302; 71/92

[56] References Cited

U.S. PATENT DOCUMENTS

| 2,809,190 | 10/1957 | Kelly et al. | 548/301 |
| 2,993,046 | 7/1961 | Bortnick et al. | 548/301 |
| 4,325,954 | 4/1982 | Maillard et al. | 548/301 |
| 4,544,754 | 10/1985 | Los | 548/301 |
| 4,709,075 | 11/1987 | Keller | 548/301 |
| 4,723,989 | 2/1988 | Buck et al. | 548/301 |
| 4,726,835 | 2/1988 | Uemura et al. | 548/301 |

FOREIGN PATENT DOCUMENTS

| 6675486 | 6/1987 | Australia | 548/30 |
| 0158000 | 10/1985 | European Pat. Off. | 548/301 |
| 57-123183 | 7/1982 | Japan | 548/301 |

Primary Examiner—Mary C. Lee
Assistant Examiner—Robert C. Whittenbaugh
Attorney, Agent, or Firm—Birch, Stewart, Kolasch & Birch

[57] ABSTRACT

A butenoic acid derivative of the formula:

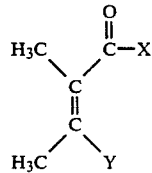

which is useful as a herbicide.

25 Claims, 1 Drawing Sheet $^1$H-NMR 60 MHz in CDCl$_3$ $^1$H-NMR 60 MHz in CDCl$_3$

BUTENOIC ACID DERIVATIVES AND USE AS HERBICIDES

The present invention relates to butenoic acid derivatives, and their production.

The present butenoic acid derivatives of the invention are represented by the following formula:

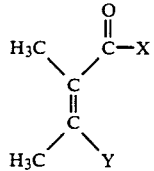
(I)

wherein
X is a hydroxyl group;
a group of the formula: —OE$^1$
wherein E$^1$ is a C$_1$–C$_8$ alkyl group, a C$_3$–C$_{12}$ alkenyl group, a C$_3$–C$_{10}$ alkynyl group, a C$_1$–C$_{12}$ alkoxy(C$_1$–C$_{12}$)alkyl group, a halo(C$_1$–C$_{12}$)alkyl group, a phenyl(C$_1$–C$_{12}$)alkyl group optionally substituted with one or more C$_1$–C$_{12}$ alkyl group on the benzene ring or a phenoxy(C$_1$–C$_{12}$)alkyl group optionally substituted with one or more C$_1$–C$_{12}$ alkyl groups on the benzene ring or a salt-forming cation selected from the group consisting of ammonium, organic ammonium, alkali metals, alkaline earth metals, manganese (II), copper (II), iron (II), iron (III), zinc (II), cobalt (II), lead (II), silver (I), aluminium (III) and nickel (II);
a group of the formula:

wherein E$^2$ is a hydrogen atom, a hydroxyl group, a
C$_1$–C$_{12}$ alkyl group, a C$_3$–C$_6$ cycloalkyl group, a
C$_1$–C$_3$ alkoxy(C$_1$–C$_{12}$)alkyl group, a
hydroxy-(C$_1$–C$_{12}$)alkyl group,
a cyano(C$_1$–C$_{12}$)alkyl group, a
C$_3$–C$_{12}$ alkenyl group, a C$_3$–C$_{12}$ alkynyl group, a carbamoyl(C$_1$–C$_{12}$)alkyl group, an aryl(C$_1$–C$_4$)alkyl
group, a C$_1$–C$_3$ alkoxycarbonyl(C$_1$–C$_{12}$)alkyl group
or a tetrahydrofurfuryl group;
or either one of the following groups:

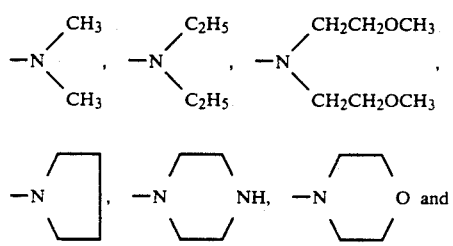

-continued

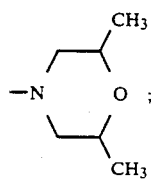

Y is either one of the following formulas:

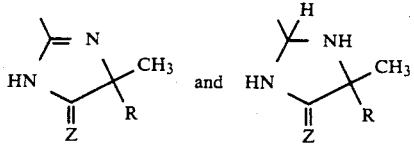

wherein Z is an oxygen atom or a sulfur atom and
R is an ethyl group, an isopropyl group or a cyclopropyl group, or their salt forms;
or X and Y may be combined together to represent either one of the following formulas:

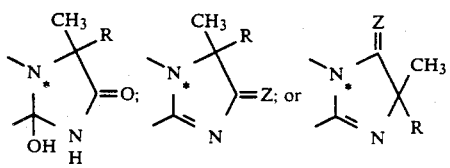

wherein Z and R are each as defined above and a nitrogen atom bearing an asterisk (*) is bonded to the carbonyl carbon atom;
with the provisos that
i) when E$^1$ is a C$_1$–C$_8$ alkyl group, a C$_3$–C$_{12}$ alkenyl group, a C$_3$–C$_{10}$ alkynyl group, a C$_1$–C$_{12}$ alkoxy(C$_1$–C$_{12}$)alkyl group, a halo(C$_1$–C$_{12}$)alkyl group, a phenyl(-C$_1$–C$_{12}$)alkyl group optionally substituted with one or more C$_1$–C$_{12}$ alkyl groups on the benzene ring or a phenoxy(C$_1$–C$_{12}$)alkyl group optionally substituted with one or more C$_1$–C$_{12}$ alkyl group on the benzene ring, Y represents a group of the formula:

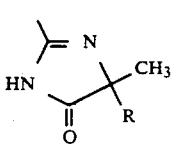

wherein R is as defined above;
ii) when E$^1$ is the salt-forming cation selected from the group consisting of ammonium, organic ammonium, alkali metals, alkaline earth metals, manganese (II), copper (II), iron (II), iron (III), zinc (II), cobalt (II), lead (II), silver (I), aluminium (III) and nickel (II), Y represents a compound of the formula:

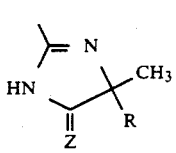

wherein R and Z are each as defined above; and
iii) when X is either one of the following formulas:

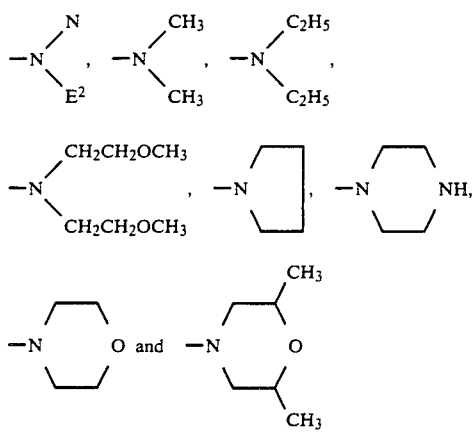

wherein $E^2$ is as defined above, Y represents a compound of the formula:

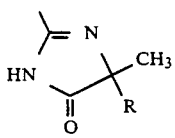

wherein R is as defined above.

The butenoic acid derivatives (I) exhibit a noticeable combatting or controlling activity on undesired vegetation of weeds in agricultural or non-agricultural fields. The compounds (I) they show an excellent herbicidal potency against various weeds in foliar treatment or soil treatment. Noticeably, some of them do not exert any substantial chemical injury to important crop plants such as cotton, soybean, corn and wheat in plowed fields, especially to cotton in plowed fields by soil treatment. Further, they can be used as total herbicides in the non-plowed fields.

The weeds against which the butenoic acid derivatives (I) can exert their herbicidal activity include broad-leaved weeds, Graminaceous weeds, Commelinaceous weeds and Cyperaceous weeds in upland fields as well as weeds in paddy fields. Examples of broad-leaved weeds are wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*sida spinosa*), field pansy (*Viola arvensis*), cleavers (*Galium aparine*), ivyleaf morningglory (*Ipomoea hederacea*), tall morningglory (*Pharbitis purpurea*), field bindweed (*Convolvulus arvensis*), purple deadnettle (*Lamium purpureum*), henbit (*Lamium amplexicaure*), jimsonweed (*Datura stramonium*), black nightshade (*Solanum nigrum*), persian speedwell (*Veronica persica*), common cocklebur (*Xanthium strumarium*), common sunflower (*Helianthus annuus*), scentless chamomile (*Matricaria perforata*), corn marigold (*Chrysanthemum segetum*), etc. Examples of Graminaceous weeds are Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), bermudagrass (*Cynodon dactylon*), etc; Commelinaceous weeds include asiatic dayflower (*Commelina communis*), etc. Examples of Cyperaceous weeds are rice flatsedge (*Cyperus iria*), purple nutsedge (*Cyperus rotundus*), etc.

Among the butenoic acid derivatives (I), some specific examples of the preferred compounds are as follows: 5-hydroxy-2-isopropyl-2,6,7-trimethyl-4H-1,4-diazabicyclo-[3.3.0]oct-6-ene-3,8-dione (Compound No. 2), 2-methyl-3-(5'-isopropyl-5'-methyl-4'-oxo-2'-imidazolin-2'-yl)-(Z)-2-butenoic acid (Compound No. 17), 2-isopropyl-2,6,7-tri-methyl-1,4-diazabicyclo[3.3.0]oct-4,6-diene-3,8-dione (Compound No. 22), 2-methyl-3-(trans-5'-isopropyl-5'-methyl-4'-thioxoimidazolidin-2'-yl)-(Z)-2-butenoic acid (Compound No. 82 (trans)), aluminium 2-methyl-3-(5'-iso-propyl-5'-methyl-4'-oxo-2'-imidazolin-2'-yl)-(Z)-2-butenoate (Compound No. 41), 2-methyl-3-(trans-5'-isopropyl-5'-methyl-4'-oxoimidazolidin-2'-yl)-(Z)-2-butenoic acid (Compound No. 81 (trans)), 2-methyl-3-(5'-isopropyl-5'-methyl-4'-oxo-2'-imidazolin-2'-yl)-(Z)-2-butenoic acid amide (Compound No. 55).

The butenoic acid derivatives (I) can be produced by various procedures, of which typical examples are set forth below.

Procedure (A):

The butenoic acid derivative (I) wherein X and Y are combined together to represent a group of the formula:

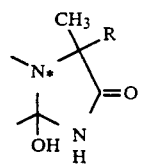

wherein R is as defined above, i.e. the butenoic acid derivative of the formula:

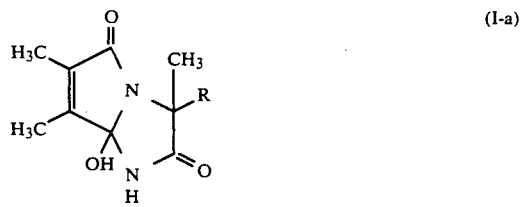 (I-a)

wherein R is as defined above, can be prepared by reacting a dioxopyrroline compound of the formula:

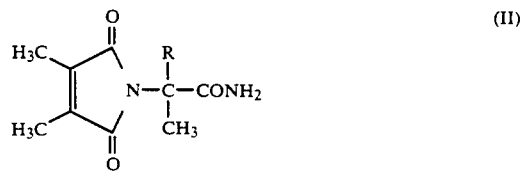 (II)

wherein R is as defined above with a base in a solvent at a temperature of 0° C. to 100° C. for a period of 0.5 to 24 hours. The base is usually employed in an amount of 1 to 10 equivalents to 1 equivalent of the dioxypyrroline compound (II). As the base, an inorganic base such as sodium hydroxide or potassium hydroxide may be used. Examples of the solvent are alcohols (e.g. methanol, ethanol), ethers (e.g. dioxane), water, etc.

Recovery of the reaction product from the reaction mixture may be accomplished, for instance, by acidifying the reaction mixture and collecting the precipitated crystals by filtration, or extracting the acidified mixture with an organic solvent and concentrating the extract. When desired, the reaction product thus recovered may be subjected to purification by chromatography or recrystallization.

Examples of the butenoic acid derivatives (I-a) obtainable by the above procedure are shown in Table 1.

TABLE 1

(I-a)

$$\text{H}_3\text{C} \begin{array}{c} \text{O} \\ \parallel \\ \end{array} \text{N} - \begin{array}{c} \text{CH}_3 \\ \text{R} \\ \end{array}$$

(structure shown)

| Compound No. | R | Physical property |
|---|---|---|
| 1 | $C_2H_5$ | m.p., 153–155° C. |
| 2 | $i\text{-}C_3H_7$ | m.p., 183–185° C. |
| 3 | $-CH\begin{array}{c}CH_2\\ \diagdown \\ CH_2\end{array}$ | m.p., 178–180° C. |

Some practical embodiments of production of the butenoic acid derivatives (I-a) are as follows:

EXAMPLE 1

A suspension of alpha-isopropyl-alpha-methyl-(2,5-dioxo-3,4-dimethyl-3-pyrroline)-1-acetamide (1.5 g) in 30% aqueous sodium hydroxide solution (8 ml) was stirred at 80° C. for 2.5 hours and allowed to cool to room temperature. The reaction mixture was acidified with conc. hydrochloric acid under ice-cooling. The precipitated crystals were collected by filtration and dried. Purification of the collected crystals by chromatography on silica gel with a mixture of hexane and acetone as an eluent gave 300 mg of 5-hydroxy-2-isopropyl-2,6,7-trimethyl-4H-1,4-diazabicyclo[3.3.0]-oct-6-ene-3,8-dione (Compound No. 2). m.p., 183° C.–185° C..

IR (nujol) cm$^{-1}$: 3328, 3200, 3112, 1726, 1750. Mass spectrum CI $(M+1)^+$, 239; EI $(M-18)^+$, 220.

EXAMPLE 2

A suspension of alpha-isopropyl-alpha-methyl-(2,5-dioxo-3,4-dimethyl-3-pyrroline)-1-acetamide (3.0 g) in 40% aqueous sodium hydroxide solution (5 ml) was stirred at 60° C. for 1 hour. The reaction mixture was acidified with conc. hydrochloric acid under ice-cooling, extracted with chloroform and dried over sodium sulfate. Chloroform was removed by distillation, and the residue was recrystallized from acetonitrile to give 280 mg of 5-hydroxy-2-isopropyl-2,6,7-trimethyl-4H-1,4-diazabicyclo [3.3.0]oct-6-ene-3,8dione (Compound No. 2). m.p. 183° C.–185° C.

Procedure (B):

The butenoic acid derivative (I) wherein X is a group of the formula: $-OE^1$ (in which $E^1$ is a $C_1$–$C_8$ alkyl group, a $C_3$–$C_{12}$ alkenyl group, a $C_3$–$C_{10}$ alkynyl group, a $C_1$–$C_{12}$ alkoxy($C_1$–$C_{12}$)alkyl group, a halo($C_1$–$C_{12}$)alkyl group, a phenyl($C_1$–$C_{12}$)alkyl group optionally substituted with one or more $C_1$–$C_{12}$ alkyl on the benzene ring or a phenoxy-($C_1$–$C_{12}$)alkyl group optionally substituted with one or more $C_1$–$C_{12}$ alkyl groups) and Y is a group of the formula:

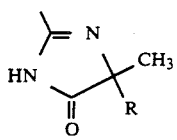

wherein R is as defined above, i.e. the butenoic acid derivative of the formula:

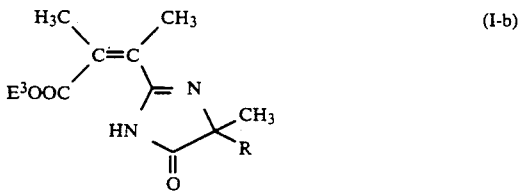

wherein R is as defined above and $E^3$ is a $C_1$–$C_8$ alkyl group, a $C_3$–$C_{12}$ alkenyl group, a $C_3$–$C_{10}$ alkynyl group, a $C_1$–$C_{12}$ alkoxy($C_1$–$C_{12}$)alkyl group, a halo($C_1$–$C_{12}$)alkyl group or a phenyl($C_1$–$C_{12}$)alkyl group optionally substituted with one or more $C_1$–$C_{12}$ alkyl groups or a phenoxy($C_1$–$C_{12}$)alkyl group optionally substituted with one or more $C_1$–$C_{12}$ alkyl groups can be produced by reacting a maleamide compound of the formula:

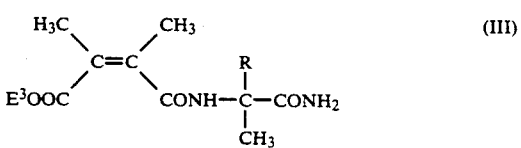

wherein R and $E^3$ are each as defined above with phosphorus pentachloride for dehydrative cyclization, followed by neutralization with a base.

The dehydrative cyclization may be performed in a solvent at a temperature of from room temperature to 120° C. for a period of 10 minutes to 24 hours. The phosphorus pentachloride and the base are employed respectively in amounts of 1 to 5 equivalents and of not less than 2 equivalents to 1 equivalent of the maleamide (III). As the solvent, there may be exemplified aromatic hydrocarbons (e.g. benzene, toluene, xylene), halogenated hydrocarbons (e.g. chloroform, carbon tetrachloride, dichloroethane, chlorobenzene, dichlorobenzene), etc. Examples of the base are sodium hydrogencarbonate, sodium carbonate, potassium carbonate, etc. These bases are usually employed in the form of an aqueous solution.

Recovery of the reaction product from the reaction mixture is normally accomplished by concentration of the organic layer containing the reaction product, if necessary, with previous drying or azeotropic dehydration. The recovered product may be purified by a per se conventional purification procedure such as chromatography or recrystallization.

Examples of the butenoic acid derivatives (I-b) as can be produced by the above procedure are shown in Table 2.

TABLE 2

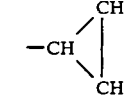

(I-b)

| E³ | R |
|---|---|
| CH₃ | C₂H₅ |
| CH₃ | i-C₃H₇ |
| CH₃ | —CH(CH₂)(CH₂) (cyclopropyl) |
| C₂H₅ | C₂H₅ |
| C₂H₅ | i-C₃H₇ |
| C₂H₅ | —CH(CH₂)(CH₂) |
| n-C₃H₇ | C₂H₅ |
| n-C₃H₇ | i-C₃H₇ |
| n-C₃H₇ | —CH(CH₂)(CH₂) |
| i-C₃H₇ | C₂H₅ |
| i-C₃H₇ | i-C₃H₇ |
| i-C₃H₇ | —CH(CH₂)(CH₂) |
| n-C₄H₉ | C₂H₅ |
| n-C₄H₉ | i-C₃H₇ |
| n-C₄H₉ | —CH(CH₂)(CH₂) |
| n-C₅H₁₁ | C₂H₅ |
| n-C₅H₁₁ | i-C₃H₇ |
| n-C₅H₁₁ | —CH(CH₂)(CH₂) |
| i-C₅H₁₁ | C₂H₅ |
| i-C₅H₁₁ | i-C₃H₇ |
| i-C₅H₁₁ | —CH(CH₂)(CH₂) |
| n-C₆H₁₃ | C₂H₅ |
| n-C₆H₁₃ | i-C₃H₇ |

TABLE 2-continued

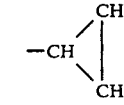

(I-b)

| E³ | R |
|---|---|
| n-C₆H₁₃ | —CH(CH₂)(CH₂) |
| CH₂=CHCH₂ | C₂H₅ |
| CH₂=CHCH₂ | i-C₃H₇ |
| CH₂=CHCH₂ | —CH(CH₂)(CH₂) |
| CH₂=C(CH₃)—CH₂ | C₂H₅ |
| CH₂=C(CH₃)—CH₂ | i-C₃H₇ |
| CH₂=C(CH₃)—CH₂ | —CH(CH₂)(CH₂) |
| CH₂=CH—CH=CH—CH₂ | C₂H₅ |
| CH₂=CH—CH=CH—CH₂ | i-C₃H₇ |
| CH₂=CH—CH=CH—CH₂ | —CH(CH₂)(CH₂) |
| CH≡C—CH₂ | C₂H₅ |
| CH≡C—CH₂ | i-C₃H₇ |
| CH≡C—CH₂ | —CH(CH₂)(CH₂) |
| CH≡C—CH(CH₃) | C₂H₅ |
| CH≡C—CH(CH₃) | i-C₃H₇ |
| CH≡C—CH(CH₃) | —CH(CH₂)(CH₂) |
| CH≡C—CH₂—CH₂ | C₂H₅ |
| CH≡C—CH₂—CH₂ | i-C₃H₇ |
| CH≡C—CH₂—CH₂ | —CH(CH₂)(CH₂) |

TABLE 2-continued $$\text{(I-b)}$$

Structure: H₃C and CH₃ on C=C; E³OOC on one side, N on other; connected through C=N to C(CH₃)(R) with HN-C(=O) ring closure (imidazolinone).

| E³ | R |
|---|---|
| CH₃OCH₂CH₂ | C₂H₅ |
| CH₃OCH₂CH₂ | i-C₃H₇ |
| CH₃OCH₂CH₂ | —CH(CH₂CH₂) (cyclopropyl) |
| ClCH₂CH₂ | C₂H₅ |
| ClCH₂CH₂ | i-C₃H₇ |
| ClCH₂CH₂ | —CH(CH₂CH₂) (cyclopropyl) |
| C₆H₅—CH₂ | C₂H₅ |
| C₆H₅—CH₂ | i-C₃H₇ |
| C₆H₅—CH₂ | —CH(CH₂CH₂) (cyclopropyl) |
| t-C₄H₉—C₆H₄—CH₂ | C₂H₅ |
| t-C₄H₉—C₆H₄—CH₂ | i-C₃H₇ |
| t-C₄H₉—C₆H₄—CH₂ | —CH(CH₂CH₂) (cyclopropyl) |
| C₆H₅—(CH₂)₃ | C₂H₅ |
| C₆H₅—(CH₂)₃ | i-C₃H₇ |
| C₆H₅—(CH₂)₃ | —CH(CH₂CH₂) (cyclopropyl) |
| C₆H₅—O(CH₂)₃ | C₂H₅ |
| C₆H₅—O(CH₂)₃ | i-C₃H₇ |
| C₆H₅—O(CH₂)₃ | —CH(CH₂CH₂) (cyclopropyl) |

Some practical embodiments of production of the butenoic acid derivatives (I-b) are as follows:

EXAMPLE 3

To a suspension of crude crystals of N-(2,3-di- methylbutanamido-2-yl)-2,3-dimethylmaleamidic acid ethyl ester (5.6 g) in toluene (200 ml), phosphorus pentachloride (8.0 g) was added, and the resultant mixture was stirred at 90° C. for 1 hour. The reaction mixture was allowed to cool to room temperature and neutralized with an aqueous sodium hydrogencarbonate solution. The organic layer was dried over anhydrous magnesium sulfate and concentrated. The residue was purified by chromatography on silica gel to give 1.84 g of ethyl 2-methyl-3-(5'-isopropyl-5'-methyl-4'-oxo-2'-imidazolin-2'-yl)-(Z)-2-butenoate (Compound No. 5). m.p., 65° C.–68° C. (Immediately after production, the product was in an oil state ($n_D^{23.0}$ 1.5010); when allowed to stand at room temperature for one week, the oil converted into crystals having the melting point.)

In the same manner as above, the butenoic acid derivatives (I-b) as shown in Table 3 could be produced.

TABLE 3

$$\text{(I-b)}$$

| Compound No. | E⁴ | R | Physical property |
|---|---|---|---|
| 4 | CH₃ | i-C₃H₇ | $n_D^{22.0}$ 1.4932 |
| 5 | C₂H₅ | i-C₃H₇ | $n_D^{23.0}$ 1.5010 |
| 6 | n-C₃H₇ | i-C₃H₇ | $n_D^{18.0}$ 1.5300 |
| 7 | i-C₃H₇ | i-C₃H₇ | $n_D^{23.0}$ 1.5128 |

TABLE 3-continued (I-b)

H₃C\  /CH₃
   C=C
E⁴OOC/  \\=N
         \\
         HN—C(CH₃)(R)
          ‖
          O

| Compound No. | E⁴ | R | Physical property |
|---|---|---|---|
| 8 | n-C₄H₉ | i-C₃H₇ | $n_D^{18.0}$ 1.4910 |
| 9 | n-C₅H₁₁ | i-C₃H₇ | $n_D^{18.0}$ 1.5110 |
| 10 | i-C₅H₁₁ | i-C₃H₇ | $n_D^{24.5}$ 1.4791 |
| 11 | n-C₆H₁₃ | i-C₃H₇ | $n_D^{24.5}$ 1.4730 |
| 12 | CH₂=CHCH₂ | i-C₃H₇ | $n_D^{21.0}$ 1.4895 |
| 13 | C₆H₅—CH₂— | i-C₃H₇ | $n_D^{21.0}$ 1.5307 |
| 14 | t-C₄H₉—C₆H₄—CH₂— | i-C₃H₇ | $n_D^{22.0}$ 1.5166 |
| 15 | C₆H₅—(CH₂)₃— | i-C₃H₇ | $n_D^{26.5}$ 1.5058 |
| 16 | C₆H₅—O(CH₂)₃— | i-C₃H₇ | $n_D^{24.5}$ 1.5194 |

Procedure (C)

The butenoic acid derivative (I) wherein X is a hydroxyl group and Y is a group of the formula:

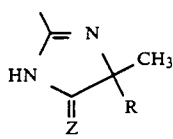

wherein R and Z are each as defined above, or its salt form, i.e. the butenoic acid derivative of the formula:

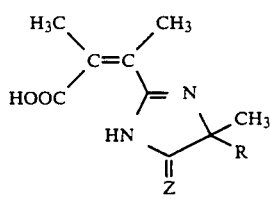
(I-c)

wherein R and Z are each as defined above, or its salt, can be prepared by reacting a maleamide compound of the formula:

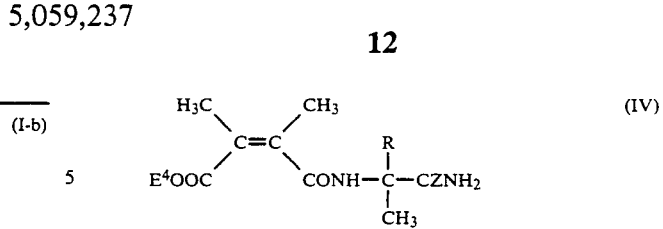
(IV)

wherein R and Z are each as defined above and D⁴ is a quaternary ammonium cation or an alkali metal cation with a base in a solvent, followed by acidification.

The quaternary ammonium cation may be the one originated from a tertiary amine such as triethylamine, 1,8-diazabicyclo[5.4.6]undeca-7-ene (DBU), 1,4-diazabicyclo-[2.2.0]octane (Dabco), 4-dimethylaminopyridine (DMAP) or diisopropylethylamine. As the alkali metal cation, there may be exemplified sodium cation, potassium cation, etc.

The reaction may be performed at a temperature of 0° C. to 100° C. for a period of 0.5 to 24 hours. The base is normally used in an amount of from 2 to 20 equivalents, preferably from 2 to 6 equivalents to 1 equivalent of the maleamide compound (IV). As the solvent, there may be exemplified alcohols (e.g. methanol, ethanol), ethers (e.g. dioxane), water, etc. The base may be an inorganic base such as sodium hydroxide or potassium hydroxide. The acidification may be made by the use of an acid such as hydrochloric acid or sulfuric acid.

Recovery of the reaction product from the reaction mixture may be accomplished by collecting such product precipitated as crystals by filtration or by extracting such product dissolved in the reaction mixture with any suitable solvent and concentrating the resultant extract. The thus recovered product may be, if necessary, purified by a per se conventional purification procedure such as column chromatography or recrystallization.

As the salts of the butenoic acid derivative (I-c), there are exemplified hydrochloride, hydrobromide, etc. These salts may be prepared, for instance, by introducing gaseous hydrogen chloride or hydrogen bromide into a solution of the butenoic acid derivative (I-c) in a solvent such as a halogenated hydrocarbon (e.g. methylene chloride, chlorobenzene, dichlorobenzene) or an ether (e.g. diethyl ether, dioxane, tetrahydrofuran), usually at a temperature of 0° C. to 50° C. for a period of 0.5 to 5 hours. The amount of hydrogen chloride or hydrogen bromide to be introduced may be 'equivalent or more to 1 equivalent of the butenoic acid derivative (I-c). The produced salt can be recovered from the reaction mixture, for instance, by filtering and drying. Further purification may be achieved by recrystallization or any other conventional procedure.

Examples of the butenoic acid derivatives (I-c) and their salts are shown in Table 4.

TABLE 4

(I-c)

H₃C\  /CH₃
   C=C
HOOC/  \\=N
         \\
         HN—C(CH₃)(R)
          ‖
          Z

| Z | R | Form of salt |
|---|---|---|
| O | C₂H₅ | Free |
| O | C₂H₅ | Hydrochloride |
| O | C₂H₅ | Hydrobromide |
| O | i-C₃H₇ | Free |

TABLE 4-continued (I-c)

structure with H3C, CH3, C=C, HOOC, N, HN, CH3, R, Z

| Z | R | Form of salt |
|---|---|---|
| O | i-C₃H₇ | Hydrochloride |
| O | i-C₃H₇ | Hydrobromide |
| O | —CH(CH₂CH₂) (cyclopropyl) | Free |
| O | —CH(CH₂CH₂) | Hydrochloride |
| O | —CH(CH₂CH₂) | Hydrobromide |
| S | C₂H₅ | Free |
| S | C₂H₅ | Hydrochloride |
| S | C₂H₅ | Hydrobromide |
| S | i-C₃H₇ | Free |
| S | i-C₃H₇ | Hydrochloride |
| S | i-C₃H₇ | Hydrobromide |
| S | —CH(CH₂CH₂) | Free |
| S | —CH(CH₂CH₂) | Hydrochloride |
| S | —CH(CH₂CH₂) | Hydrobromide |

Some practical embodiments of production of the butenoic acid derivatives (I-c) are as follows:

EXAMPLE 4

Triethylamine salt of N-(alpha-isopropyl-alpha-methyl-alpha-carbamoylmethyl)-2,3-dimethylmaleamidic acid (4.5 g) was added to a 30% sodium hydroxide solution (6 ml), and the reaction was carried out at 80° C. for 1.5 hours. The reaction mixture was acidified with conc. hydrochloric acid under cooling. The precipitated crystals were collected by filtration, dried and then dissolved in methanol. After removal of sodium chloride by filtration, the filtrate was concentrated to eliminate the solvent, whereby 3.1 g of 2-methyl-3-(5'-isopropyl-5'-methyl-4'-oxo- 2'-imidazolin-2'-yl)-(Z)-2-butenoic acid (Compound No. 17) were obtained m.p., 215° C.-217° C. (decomp.).

IR (nujol) cm⁻¹: 1788, 1720, 1670, 1618.

EXAMPLE 5

Triethylamine salt of N-(alpha-ethyl-alpha-methyl-alpha-carbamoylmethyl)-2,3-dimethylmaleamidic acid (8.0 g) was added to a 30% sodium hydroxide solution (9 ml), and the reaction was carried out at 80° C. to 85° C. for 2 hours. The reaction mixture was acidified with conc. hydrochloric acid under cooling. The precipitated crystals were collected by filtration, washed with cold water and dried to give 3.8 g of 2-methyl-3-(5'-ethyl-5'-methyl-4'-oxo-2'-imidazolin-2'-yl)-(Z)-2-butenoic acid (Compound No. 18). m.p., 146° C.-148° C.

EXAMPLE 6

Triethylamine salt of N-(alpha-cyclopropyl-alpha-methyl-alpha-carbamoylmethyl)-2,3-dimethylmaleamidic acid (10.0 g) was added to a 30% sodium hydroxide solution (10 ml), and the reaction was carried out at 80° C. for 3 hours. The reaction mixture was acidified with conc. hydrochloric acid under cooling. The precipitated crystals were collected by filtration, washed with a small amount of cold water and dried to give 4.5 g of 2-methyl-3-(5'-cyclopropyl-5'-methyl-4'-oxo-2'-imidazolin-2'-yl)-(Z)-2-butenoic acid (Compound No. 19). m.p., 164.3° C.

EXAMPLE 7

1,8-Diazabicyclo[5.4.0]undeca-7-ene (DBU) salt of N-(alpha-isopropyl-alpha-methyl-alpha-thiocarbamoylmethyl)-2,3-dimethylmaleamidic acid (10.5 g) was added to a 30% sodium hydroxide solution (10 ml), and the reaction was carried out at 80° C. for 2.5 hours. The reaction mixture was acidified with conc. hydrochloric acid under cooling, and the precipitated crystals were collected by filtration, washed with cold water (20 ml) and dried under reduced pressure to give 3.79 g of 2-methyl-3-(5'-isopropyl-5'-methyl-4'-thioxo-2'-imidazolin-2'-yl)-(Z)-2-butenoic acid (Compound No. 20). Carbonized above 175° C.

EXAMPLE 8

Into a suspension of 2-methyl-3-(5'-isopropyl-5'-methyl-4'-oxo-2'-imidazolin-2'-yl)-(Z)-2-butenoic acid (1.0 g) in methylene chloride (250 ml), hydrogen chloride gas was introduced at room temperature for 30 minutes. The produced hydrochloride was collected by filtration through a glass filter and dried under reduced pressure to give 840 mg of 2-methyl-3-(5'-isopropyl-5'-methyl-4'-oxo-2'-imidazolin-2'-yl)-(Z)-2-butenoic acid hydrochloride (Compound No. 21). m.p., 227° C. (decomp.).

Procedure (D)

The butenoic acid derivative (I) wherein X and Y are combined together to represent either one of the following formulas:

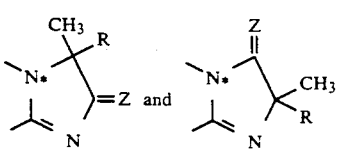

wherein R and Z are each as defined above, i.e. the butenoic acid derivative of either one of the formulas:

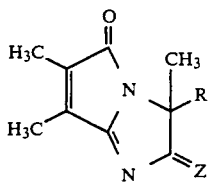

(I-d)

and

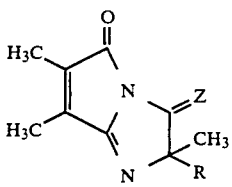

(I-d')

wherein R and Z are each as defined above can be prepared by subjecting the butenoic acid derivative (I-a) or the butenoic acid derivative of the formula:

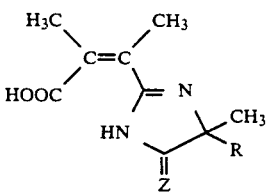

(I-c)

wherein R and Z are each as defined above to ring-closure in the molecule.

The ring-closure may be accomplished by (i) reacting the butenoic acid derivative (I-a) or (I-c) wherein Z is an oxygen atom with thionyl chloride, phosphorus oxychloride or acetic anhydride in the presence of a base at a temperature of about $-10$ to $150°$ C. for a period of about 30 minutes to 10 hours, or (ii) reacting the butenoic acid derivative (I-a) or (I-c) wherein Z is an oxygen atom with trifluoroacetic anhydride at a temperature of about $-40°$ C. to room temperature for a period of about 30 minutes to 10 hours. In each of these reactions (i) and (ii), dehydrative condensation takes place. As the base, there may be used pyridine, triethylamine, sodium acetate, potassium acetate, etc. The reaction can proceed in the absence of any solvent, but it is usually preferred to effect the reaction in an inert solvent, of which examples are halogenated hydrocarbons (e.g. methylene chloride, chloroform, carbon tetrachloride, dichloroethane), acetonitrile, aromatic hydrocarbons (e.g. benzene, toluene), etc.

The ring-closure may be also accomplished by (iii) reacting the butenoic acid derivative (I-c) with dicyclohexylcarbodiimide (DCC) for dehydrative condensation.

Further, the ring-closure may be accomplished by (iv) reacting the butenoic acid derivative (I-c) wherein Z is an oxygen atom with a halogen compound of the formula:

$$Q-W \quad (V)$$

wherein Q is a halogen atom, W is a $C_1-C_8$ alkyl group, a $C_3-C_{10}$ alkenyl group or a $C_3-C_{10}$ alkynyl group in the presence of a base at a temperature of about room temperature (ca. $20°$ C.) to $150°$ C. for a period of about 1 to 24 hours, or (v) reacting the butenoic acid derivative (I-c) with a chloroformic ester in the presence of a base at a temperature of about $0°$ C. to $150°$ C. for a period of about 10 minutes to 24 hours. As the halogen compound (V), there may be exemplified $C_1-C_8$ chloroalkanes, $C_1-C_8$ bromoalkanes, $C_1-C_8$ iodoalkanes, $C_3-C_{10}$ chloroalkenes in which the chlorine atom does not attach to the carbon atom having a double bond, $C_3-C_{10}$ bromoalkenes in which the bromine atom does not attach to the carbon atom having a double bond, $C_3-C_{10}$ iodoalkenes in which the iodine atom does not attach to the carbon atom having a double bond, $C_3-C_{10}$ chloroalkynes in which the chlorine atom does not attach to the carbon atom having the triple bond, $C_3-C_{10}$ bromoalkynes in which the bromine atom does not attach to the carbon atom having the triple bond, $C_3-C_{10}$ iodoalkynes in which the iodine atom does not attach to the carbon atom having the triple bond, etc. Typical examples of the base are potassium carbonate for the reaction (iv) mad triethylamine for the reactions (v). The reaction (iv) may be accelerated by the use of a phase transfer catalyst (e.g. tetra-n-butyl ammonium bromide).

Post treatment of the reaction mixture may be performed by a per se conventional procedure. In case of the reaction (i) using thionyl chloride or phosphorus oxychloride, for instance, the reaction mixture is poured into ice-water, extracted with an organic solvent and concentrated to give the product. In case of the reaction (i) or (ii) with acetic anhydride or trifluoroacetic anhydride, the reaction mixture is concentrated under reduced pressure, optionally followed by recrystallization or chromatography for purification. The reaction mixture in the reaction (iv) or (v) may be extracted with an organic solvent, followed by concentration. When desired, the product may be purified by chromatography, recrystallization or the like.

As the reaction product, there is obtainable the butenoic acid derivative (I-d) or (I-d') or their mixture depending upon the reaction as adopted. For instance, the reaction (iv) selectively affords the butenoic acid derivative (I-d) wherein Z is an oxygen atom. Further, for instance, the reaction (v) affords the butenoic acid derivative (I-d') rich product, usually the weight proportion of the butenoic acid derivative (I-d'): the butenoic acid derivative (I-d) therein being from about 2:1 to 9:1. In case of the reaction (v), it is possible to increase the content of the butenoic acid derivative (I-d') in the product by removing the butenoic acid derivative (I-d) with fractional crystallization.

In the manner as illustrated above, the butenoic acid derivatives (I-d) and (I-d') as shown in Tables 5 and 6 are obtainable.

TABLE 5

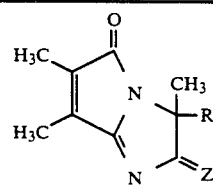

(I-d)

| R | Z |
|---|---|
| $C_2H_5$ | O |
| $i-C_3H_7$ | O |

TABLE 5-continued (I-d)

[Structure: pyrrole-type ring with H3C groups, N-CH3, -R, N=Z substituents]

| R | Z |
|---|---|
| -CH(CH2)(CH2) [cyclopropyl] | O |
| C2H5 | S |
| i-C3H7 | S |
| -CH(CH2)(CH2) [cyclopropyl] | S |

TABLE 6

(I-d')

[Structure with H3C groups, N, Z, CH3, R substituents]

| R | Z |
|---|---|
| C2H5 | O |
| i-C3H7 | O |
| -CH(CH2)(CH2) [cyclopropyl] | O |
| C2H5 | S |
| i-C3H7 | S |
| -CH(CH2)(CH2) [cyclopropyl] | S |

Some practical embodiments for production of the butenoic acid derivatives (I-d) and (I-d') or their mixture are as follows:

EXAMPLE 9

To a suspension of 2-methyl-3-(5'-isopropyl-5'-methyl-4'oxo-2'imidazolin-2'-yl)-(Z)-2-butenoic acid (4.9 g) in acetonitrile (100 ml), acetic anhydride (10.0 g) and anhydrous potassium acetate (600 mg) were added, and the resultant mixture was refluxed while stirring for 4 hours. The reaction mixture was concentrated under reduced pressure, and the residue was dissolved in chloroform, followed by washing with an aqueous sodium hydrogencarbonate solution and water in this order. The washed solution was dried over anhydrous magnesium sulfate, and chloroform was removed by distillation to give a mixture (2.90 g) of 2-isopropyl-2,6,7-trimethyl-1,4-diazabicyclo[3.3.0]oct-4,6-diene-3,8-dione (Compound No. 22) and 3-isopropyl-3,6,7-trimethyl-1,4-diazabicyclo[3.3.0]oct-4,6-diene-2,8-dione (Compound No. 23) as a waxy product. m.p., 75° C.-78° C. and 130° C.-133° C. (observed twice).

NMR δ (CDCl$_3$) (ppm): 0.85-1.24 (6H, m), 2.00-2.20 (6H, m), 1.48 (s, H in methyl at 2-position of the 3,8-dione compound), 1.52 (s, H in methyl at 3-position of the 2,8-dione compound).

Gas chromatography: mixing proportion (percentage at area), Compound No. 22, 64.3%; Compound No. 23, 35.7%. The conditions for gas chromatography were as follows: F.I.D. gas chromatography; column, SE-30, 5%, 1.5 m; column temperature, 170° C. (constant); injection, 220° C.; air, 1.5 kg/cm$^2$; H$_2$, 1.0 kg/cm$^2$; N$_2$, 0.4 kg/cm$^2$. Retention time: Compound No. 22, 9.39 min., Compound No. 23, 10.26 min.

In the same manner as above but using trifluoroacetic acid instead of acetic anhydride, there was produced 2-isopropyl-2,6,7-trimethyl-1,4-diazabicyclo[3.3.0]oct-4,6-diene-3-thion-8-one (Compound No. 24) from 2-methyl-3-(5'-isopropyl-5'-methyl-4'-thioxo-2'-imidazolin-2'-yl)-(Z)-2-butenoic acid. m.p., 111° C.-113° C.

EXAMPLE 10

Ethyl iodide (3.1 g), anhydrous potassium carbonate (3.0 g) and tetra-n-butylammonium bromide (200 mg) were added to a solution of 2-methyl-3-(5'-isopropyl-5'-methyl-4'-oxo-2'-imidazolin-2'-yl)-(Z)-2-butenoic acid (4.68 g) in acetonitrile (150 ml), and the resultant mixture was heated under reflux for 6 hours. After removal of acetonitrile, the residue was extracted with methylene chloride. The extract was washed with a 5% sodium hydroxide solution and water, dried over anhydrous magnesium sulfate and concentrated to give 2.37 g of 2-isopropyl-2,6,7-trimethyl-1,4-diazabicyclo[3.3.0]oct-4,6-diene-3,8-dione (Compound No. 22). m.p., 78° C.-80° C. The NMR chart of this product is shown in the accompanying drawing.

EXAMPLE 11

Thionyl chloride (80 mg) was added to a solution of 5-hydroxy-2-isopropyl-2,6,7-trimethyl-4H-1,4-diazabicyclo[3.3.0]oct-6-ene-3,8-dione (80 mg) in pyridine (5 ml) at a temperature of 0° C. to 5° C., and the resultant mixture was stirred for 15 minutes. The reaction mixture was washed with 5% hydrochloric acid and water, dried over anhydrous magnesium sulfate and concentrated to give 40 mg of 2-isopropyl-2,6,7-trimethyl-1,4-diazabicyclo[3.3.0]oct-4,6-diene-3,8-dione (Compound No. 22). m.p., 78° C.-80° C.

EXAMPLE 12

2-Methyl-3-(5'-isopropyl-5'-methyl-4'-oxo-2'-imidazolin-2'-yl) -(Z)-2-butenoic acid (2.5 g) and triethylamine (1.1 g) were added to tetrahydrofuran (250 ml), and ethyl chlorocarbonate (1.25 g) was dropwise added to the resultant mixture while stirring at room temperature. After the dropwise addition was completed, stirring was continued at room temperature for 2 hours. The reaction mixture was filtered with celite, and the filtrate was concentrated. The residue was dissolved in methylene chloride, washed with a 5% aqueous solution of sodium hydroxide and water, dried over anhydrous magnesium sulfate and concentrated to give an oil (1.0 g). To the oil, ether was added, followed by filtration to remove insoluble materials. The filtrate was concentrated to give an oil (610 mg). Gas chromatographic analysis revealed that the oil is a mixture (1:9) of 2-isopropyl-2,6,7-trimethyl-1,4-diazabicyclo[3.3.0]oct- 4,6-diene-3,8-dione (Compound No. 22) and 3-isopropyl-3,6,7-trimethyl-1,4-diazabicyclo[3.3.0]oct-4,6-diene-2,8-dione (Compound No. 23). $n_D^{26.1}$ 1.5269.

The conditions for gas chromatography were as follows: F.I.D. gas chromatography; column, SE-30, 5%, 1.5 m; column temperature, 170° C. (constant); injection, 220° C.; air, 0.7 kg/cm²; H₂, 0.8 kg/cm²; N₂, 0.4 kg/cm². Retention time: Compound No. 22, 7.36 min., Compound No. 23, 7.86 min.

Procedure (E)

The butenoic acid derivative (I) wherein $E^1$ is a salt-forming cation such as ammonium, organic ammonium, alkali metal, alkaline earth metal, manganese (II), copper (II), iron (II), iron (III), zinc (II), cobalt (II), lead (II), silver (I), aluminium (III) or nickel (II) and Y is a group of the formula:

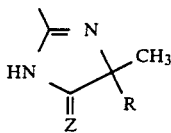

wherein R and Z are each as defined above, i.e. the butenoic acid derivative of the formula:

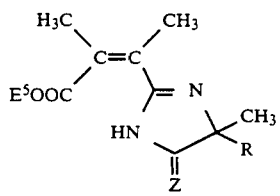

wherein R and Z are each as defined above and $E^5$ is salt-forming cation such as ammonium, organic ammonium, alkali metal, alkaline earth metal, manganese (II), copper (II), iron (II), iron (III), zinc (II), cobalt (II), lead (II), silver (I), aluminium (III) or nickel (II), can be produced by reacting the butenoic acid derivative (I-c) with a salt-forming cation-containing compound such as ammonia, an amine, a tetraalkylammonium hydroxide, a hydroxide or carbonate of an alkali metal or alkaline earth metal, manganese (II) chloride, copper (II) sulfate, iron (II) chloride, iron (III) chloride, zinc chloride, cobalt (II) chloride, lead nitrate, silver nitrate, aluminum nitrate or nickel (II) chloride.

The reaction is ordinarily carried out in the presence or absence of a solvent at a temperature of about 0° C. to 100° C. for a period of about 30 minutes to 24 hours. The amount of the salt-forming cation-containing compound may vary depending on its kind. For instance, ammonia may be used in an amount of about 1 equivalent or more to 1 equivalent of the butenoic acid derivative (I-c). Amines, tetraalkylammonium hydroxides, hydroxides or carbonate of alkali metals or alkaline earth metals or silver nitrate may be employed in an amount of about 0.5 to 1.2 equivalents to 1 equivalent of the butenoic acid derivative (I-c). Manganese (II) chloride, copper (II) sulfate, iron (II) chloride, zinc chloride, cobalt (II) chloride, lead nitrate or nickel (II) chloride and iron (III) chloride or aluminium nitrate are respectively used in amounts of about ⅓ to 3/5 equivalents and of about ⅓ to 2/5 equivalents to 1 equivalent of the butenoic acid derivative (I-c).

As the solvent, there may be used water, lower alcohols (e.g. methanol, ethanol) or their mixtures with water, ethers (e.g. dioxane, tetrahydrofuran) or their mixtures with water, etc. The butenoic acid derivative (II) is generally used in dispersing or dissolving in the solvent.

Examples of the amine are methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, cyclopentylamine, cyclohexylamine, dicyclohexylamine, piperidine, morpholine, pyrrolidine, etc. As the tetraalkylammonium hydroxide, there are exemplified trimethylbenzylammonium hydroxide and the like. Examples of the hydroxides or carbonates of alkali metals are lithium hydroxide, sodium hydroxide, potassium hydroxide, lithium carbonate, sodium carbonate, potassium carbonate, etc. Examples of the hydroxides or carbonates of alkali earth metals are magnesium hydroxide, calcium hydroxide, barium hydroxide, magnesium carbonate, calcium carbonate, barium carbonate, etc.

Upon completion of the reaction, the reaction mixture may be treated by per se conventional procedures. For instance, the solvent is removed by distillation, and the residue or precipitate is collected, optionally followed by recrystallization.

In the same manner as above, the following butenoic acid derivatives (I-e) in Table 7 can be produced.

TABLE 7

$$\begin{array}{c} H_3C \\ \diagdown \\ E^5OOC \end{array} C=C \begin{array}{c} CH_3 \\ \diagup \\ \diagdown \\ HN \end{array} N \begin{array}{c} CH_3 \\ \diagdown \\ R \\ \| \\ Z \end{array}$$ (I-e)

| $E^5$ | R | Z |
|---|---|---|
| NH₄⁺ | C₂H₅ | O |
| NH₄⁺ | i-C₃H₇ | O |
| NH₄⁺ | —CH⟨CH₂–CH₂ (cyclopropyl) | O |
| NH₄⁺ | C₂H₅ | S |
| NH₄⁺ | i-C₃H₇ | S |

TABLE 7-continued $$\begin{array}{c} H_3C \quad CH_3 \\ C=C \\ E^5OOC \qquad N \\ \qquad \diagdown \diagup \\ HN \quad CH_3 \\ \qquad \diagdown \diagup \\ \qquad C \\ \parallel \quad R \\ Z \end{array} \quad (I\text{-}e)$$

| $E^5$ | R | Z |
|---|---|---|
| $NH_4^+$ | —CH(CH$_2$)(CH$_2$) cyclopropyl | S |
| $(C_3H_5)_3N^+$ | $C_2H_5$ | O |
| $(C_3H_5)_3N^+$ | i-$C_3H_7$ | O |
| $(C_3H_5)_3N^+$ | cyclopropyl | O |
| $(C_3H_5)_3N^+$ | $C_2H_5$ | S |
| $(C_3H_5)_3N^+$ | i-$C_3H_7$ | S |
| $(C_3H_5)_3N^+$ | cyclopropyl | S |
| morpholinium NH$^+$ | $C_2H_5$ | O |
| morpholinium NH$^+$ | i-$C_3H_7$ | O |
| morpholinium NH$^+$ | cyclopropyl | O |
| morpholinium NH$^+$ | $C_2H_5$ | S |
| morpholinium NH$^+$ | i-$C_3H_7$ | S |
| morpholinium NH$^+$ | cyclopropyl | S |
| cyclohexyl-NH$_3^+$ | $C_2H_5$ | O |
| cyclohexyl-NH$_3^+$ | i-$C_3H_7$ | O |
| cyclohexyl-NH$_3^+$ | cyclopropyl | O |
| cyclohexyl-NH$_3^+$ | $C_2H_5$ | S |
| cyclohexyl-NH$_3^+$ | i-$C_3H_7$ | S |
| cyclohexyl-NH$_3^+$ | cyclopropyl | S |
| i-$C_3H_7NH_3^+$ | $C_2H_5$ | O |
| i-$C_3H_7NH_3^+$ | i-$C_3H_7$ | O |
| i-$C_3H_7NH_3^+$ | cyclopropyl | O |
| i-$C_3H_7NH_3^+$ | $C_2H_5$ | S |
| i-$C_3H_7NH_3^+$ | i-$C_3H_7$ | S |
| i-$C_3H_7NH_3^+$ | cyclopropyl | S |
| n-$C_8H_{17}NH_3^+$ | $C_2H_5$ | O |
| n-$C_8H_{17}NH_3^+$ | i-$C_3H_7$ | O |
| n-$C_8H_{17}NH_3^+$ | cyclopropyl | O |
| n-$C_8H_{17}NH_3^+$ | $C_2H_5$ | S |
| n-$C_8H_{17}NH_3^+$ | i-$C_3H_7$ | S |
| n-$C_8H_{17}NH_3^+$ | cyclopropyl | S |
| t-$C_4H_9NH_3^+$ | $C_2H_5$ | O |
| t-$C_4H_9NH_3^+$ | i-$C_3H_7$ | O |
| t-$C_4H_9NH_3^+$ | cyclopropyl | O |
| t-$C_4H_9NH_3^+$ | $C_2H_5$ | S |
| t-$C_4H_9NH_3^+$ | i-$C_3H_7$ | S |

TABLE 7-continued $$\text{(I-e)}$$

structure: $H_3C$ and $CH_3$ on a C=C, with $E^5OOC$ on one carbon and a C=N group on the other; HN connects to C(CH_3)(R)—C(=Z)—

| $E^5$ | R | Z |
|---|---|---|
| t-$C_4H_9NH_3^+$ | —CH(CH_2)(CH_2) [cyclopropyl] | S |
| $CH_2=CHCH_2NH_3^+$ | $C_2H_5$ | O |
| $CH_2=CHCH_2NH_3^+$ | i-$C_3H_5$ | O |
| $CH_2=CHCH_2NH_3^+$ | —CH(CH_2)(CH_2) | O |
| $CH_2=CHCH_2NH_3^+$ | $C_2H_5$ | S |
| $CH_2=CHCH_2NH_3^+$ | i-$C_3H_5$ | S |
| $CH_2=CHCH_2NH_3^+$ | —CH(CH_2)(CH_2) | S |
| $CH_3O(CH_2)_2NH_3^+$ | $C_2H_5$ | O |
| $CH_3O(CH_2)_2NH_3^+$ | i-$C_3H_7$ | O |
| $CH_3O(CH_2)_2NH_3^+$ | —CH(CH_2)(CH_2) | O |
| $CH_3O(CH_2)_2NH_3^+$ | $C_2H_5$ | S |
| $CH_3O(CH_2)_2NH_3^+$ | i-$C_3H_7$ | S |
| $CH_3O(CH_2)_2NH_3^+$ | —CH(CH_2)(CH_2) | S |
| C_6H_5—$CH_2N(CH_3)_3^+$ | $C_2H_5$ | O |
| C_6H_5—$CH_2N(CH_3)_3^+$ | i-$C_3H_7$ | O |
| C_6H_5—$CH_2N(CH_3)_3^+$ | —CH(CH_2)(CH_2) | O |
| C_6H_5—$CH_2N(CH_3)_3^+$ | $C_2H_5$ | S |
| C_6H_5—$CH_2N(CH_3)_3^+$ | i-$C_3H_7$ | S |
| C_6H_5—$CH_2N(CH_3)_3^+$ | —CH(CH_2)(CH_2) | S |
| $CH_3(CH_2)_{15}N(CH_3)_3^+$ | $C_2H_5$ | O |
| $CH_3(CH_2)_{15}N(CH_3)_3^+$ | i-$C_3H_7$ | O |
| $CH_3(CH_2)_{15}N(CH_3)_3^+$ | —CH(CH_2)(CH_2) | O |
| $CH_3(CH_2)_{15}N(CH_3)_3^+$ | $C_2H_5$ | S |
| $CH_3(CH_2)_{15}N(CH_3)_3^+$ | i-$C_3H_7$ | S |
| $CH_3(CH_2)_{15}N(CH_3)_3^+$ | —CH(CH_2)(CH_2) | S |
| $Na^+$ | $C_2H_5$ | O |
| $Na^+$ | i-$C_3H_7$ | O |
| $Na^+$ | —CH(CH_2)(CH_2) | O |
| $Na^+$ | $C_2H_5$ | S |
| $Na^+$ | i-$C_3H_7$ | S |
| $Na^+$ | —CH(CH_2)(CH_2) | S |
| $K^+$ | $C_2H_5$ | O |
| $K^+$ | i-$C_3H_7$ | O |
| $K^+$ | —CH(CH_2)(CH_2) | O |
| $K^+$ | $C_2H_5$ | S |
| $K^+$ | i-$C_3H_7$ | S |
| $K^+$ | —CH(CH_2)(CH_2) | S |
| $Li^+$ | $C_2H_5$ | O |
| $Li^+$ | i-$C_3H_7$ | O |
| $Li^+$ | —CH(CH_2)(CH_2) | O |
| $Li^+$ | $C_2H_5$ | S |
| $Li^+$ | i-$C_3H_7$ | S |

TABLE 7-continued $$\underset{\underset{Z}{\overset{HN}{\vert}}}{\overset{H_3C}{\underset{E^5OOC}{>}}C=C\overset{CH_3}{\underset{}{<}}}\underset{R}{\overset{CH_3}{\underset{}{>}}}$$ (I-e)

| $E^5$ | R | Z |
|---|---|---|
| Li+ | —CH(CH$_2$CH$_2$) (cyclopropyl) | S |
| ½Ca$^{2+}$ | C$_2$H$_5$ | O |
| ½Ca$^{2+}$ | i-C$_3$H$_7$ | O |
| ½Ca$^{2+}$ | —CH(CH$_2$CH$_2$) | O |
| ½Ca$^{2+}$ | C$_2$H$_5$ | S |
| ½Ca$^{2+}$ | i-C$_3$H$_7$ | S |
| ½Ca$^{2+}$ | —CH(CH$_2$CH$_2$) | S |
| ½Ba$^{2+}$ | C$_2$H$_5$ | O |
| ½Ba$^{2+}$ | i-C$_3$H$_7$ | O |
| ½Ba$^{2+}$ | —CH(CH$_2$CH$_2$) | O |
| ½Ba$^{2+}$ | C$_2$H$_5$ | S |
| ½Ba$^{2+}$ | i-C$_3$H$_7$ | S |
| ½Ba$^{2+}$ | —CH(CH$_2$CH$_2$) | S |
| ½Mn$^{2+}$ | C$_2$H$_5$ | O |
| ½Mn$^{2+}$ | i-C$_3$H$_7$ | O |
| ½Mn$^{2+}$ | —CH(CH$_2$CH$_2$) | O |
| ½Mn$^{2+}$ | C$_2$H$_5$ | S |
| ½Mn$^{2+}$ | i-C$_3$H$_7$ | S |
| ½Mn$^{2+}$ | —CH(CH$_2$CH$_2$) | S |
| ½Cu$^{2+}$ | C$_2$H$_5$ | O |
| ½Cu$^{2+}$ | i-C$_3$H$_7$ | O |
| ½Cu$^{2+}$ | —CH(CH$_2$CH$_2$) | O |
| ½Cu$^{2+}$ | C$_2$H$_5$ | S |
| ½Cu$^{2+}$ | i-C$_3$H$_7$ | S |
| ½Cu$^{2+}$ | —CH(CH$_2$CH$_2$) | S |
| ½Fe$^{2+}$ | C$_2$H$_5$ | O |
| ½Fe$^{2+}$ | i-C$_3$H$_7$ | O |
| ½Fe$^{2+}$ | —CH(CH$_2$CH$_2$) | O |
| ½Fe$^{2+}$ | C$_2$H$_5$ | S |
| ½Fe$^{2+}$ | i-C$_3$H$_7$ | S |
| ½Fe$^{2+}$ | —CH(CH$_2$CH$_2$) | S |
| ⅓Fe$^{3+}$ | C$_2$H$_5$ | O |
| ⅓Fe$^{3+}$ | i-C$_3$H$_7$ | O |
| ⅓Fe$^{3+}$ | —CH(CH$_2$CH$_2$) | O |
| ⅓Fe$^{3+}$ | C$_2$H$_5$ | S |
| ⅓Fe$^{3+}$ | i-C$_3$H$_7$ | S |
| ⅓Fe$^{3+}$ | —CH(CH$_2$CH$_2$) | S |
| ½Zn$^{2+}$ | C$_2$H$_5$ | O |
| ½Zn$^{2+}$ | i-C$_3$H$_7$ | O |
| ½Zn$^{2+}$ | —CH(CH$_2$CH$_2$) | O |
| ½Zn$^{2+}$ | C$_2$H$_5$ | S |
| ½Zn$^{2+}$ | i-C$_3$H$_7$ | S |
| ½Zn$^{2+}$ | —CH(CH$_2$CH$_2$) | S |
| ½Co$^{2+}$ | C$_2$H$_5$ | O |
| ½Co$^{2+}$ | i-C$_3$H$_7$ | O |
| ½Co$^{2+}$ | —CH(CH$_2$CH$_2$) | O |

TABLE 7-continued $$\begin{array}{c}H_3C\\ \diagdown\\ E^5OOC\end{array}C=C\begin{array}{c}CH_3\\ \diagup\\ \diagdown\end{array}\begin{array}{c}\\ \diagdown N\\ HN\diagdown\diagup\\ \parallel\quad R\\ Z\end{array}CH_3\qquad (I\text{-}e)$$

| E⁵ | R | Z |
|---|---|---|
| ½Co²⁺ | C₂H₅ | S |
| ½Co²⁺ | i-C₃H₇ | S |
| ½Co²⁺ | —CH(—CH₂—CH₂—) (cyclopropyl) | S |
| ½Pb²⁺ | C₂H₅ | O |
| ½Pb²⁺ | i-C₃H₇ | O |
| ½Pb²⁺ | —CH(—CH₂—CH₂—) | O |
| ½Pb²⁺ | C₂H₅ | S |
| ½Pb²⁺ | i-C₃H₇ | S |
| ½Pb²⁺ | —CH(—CH₂—CH₂—) | S |
| Ag⁺ | C₂H₅ | O |
| Ag⁺ | i-C₃H₇ | O |
| Ag⁺ | —CH(—CH₂—CH₂—) | O |
| Ag⁺ | C₂H₅ | S |
| Ag⁺ | i-C₃H₇ | S |
| Ag⁺ | —CH(—CH₂—CH₂—) | S |
| ⅓Al³⁺ | C₂H₅ | O |
| ⅓Al³⁺ | i-C₃H₇ | O |
| ⅓Al³⁺ | —CH(—CH₂—CH₂—) | O |
| ⅓Al³⁺ | C₂H₅ | S |
| ⅓Al³⁺ | i-C₃H₇ | S |
| ⅓Al³⁺ | —CH(—CH₂—CH₂—) | S |
| ½Ni²⁺ | C₂H₅ | O |
| ½Ni²⁺ | i-C₃H₇ | O |
| ½Ni²⁺ | —CH(—CH₂—CH₂—) | O |
| ½Ni²⁺ | C₂H₅ | S |
| ½Ni²⁺ | i-C₃H₇ | S |
| ½Ni²⁺ | —CH(—CH₂—CH₂—) | S |

Some practical embodiments for production of the butenoic acid derivatives (I-e) are as follows:

EXAMPLE 13

Into a mixture of methanol (50 ml) and water (10 ml), 2-methyl-3-(5'-isopropyl-5'-methyl-4'-oxo-2'-imidazolin-2'-yl)-(Z)-2-butenoic acid (4.0 g) was dissolved, and a solution of sodium hydroxide (670 mg) in water (5 ml) was added thereto, followed by stirring at room temperature for 1 hour. After distillation of aqueous methanol by the aid of a rotary evaporator, the residue was dried in vacuo to give 4.3 g of sodium 2-methyl-3-(5'-isopropyl-5'-methyl-4'-oxo-2'-imidazolin-2'-yl)-(Z)-2-butenoate (Compound No. 34). m.p., 136° C.–140° C.

EXAMPLE 14

2-Methyl-3-(5'-isopropyl-5'-methyl-4'-oxo-2'-imidazolin-2'-yl)-(Z)-2-butenoic acid (400 mg) was added to aqueous ammonia (10 ml), and the resultant mixture was stirred at room temperature for 1 hour. After concentration by the aid of a rotary evaporator, the residue was washed with acetonitrile (3 ml) and dried to give 250 mg of ammonium 2-methyl-3-(5'-isopropyl-5'-methyl-4'-oxo-2'-imidazolin-2'-yl)-(Z)-2-butenoate (Compound No. 25). m.p., 110° C.–115° C.

EXAMPLE 15

2-Methyl-3-(5'-isopropyl-5'-methyl-4'-oxo-2'imidazolin-2'-yl)-(Z)-2-butenoic acid (2.0 g) was dissolved in ethanol (50 ml), and sodium hydroxide (340 mg) and water (1 ml) were added thereto, followed by stirring for 30 minutes. A solution of aluminum nitrate (1.0 g) in water (10 ml) was added thereto, and stirring was continued for 2 hours, followed by concentration to make a volume of 4 ml. The precipitated crystals were collected by filtration, washed with water (3 ml) and dried to give 1.0 g of aluminum 2-methyl-3-(5'-isopropyl-5'-methyl-4'-oxo-2'-imidazolin-2'-yl)-(Z)-2-butenoate (Compound No. 41). m.p., 137° C.–138° C.

EXAMPLE 16

To a solution of 2-methyl-3-(5'-isopropyl-5'-methyl-4'-thioxo-2'-imidazolin-2'-yl)-(Z)-2-butenoic acid (300 mg) in methanol (20 ml), t-butylamine (90 mg) was added at room temperature, and the resultant mixture was stirred for 3 hours. After distillation of methanol, the residue was washed with a small amount of ether to give 330 mg of t-butylamine salt of 2-methyl-3-(5'-isopropyl-5'-methyl-4'-thioxo-2'-imidazolin-2'-yl)-(Z)-2-butenoic acid (Compound No. 46). m.p., 97° C.-100° C.

EXAMPLE 17

To a solution of 2-methyl-3-(5'-isopropyl-5'-methyl-4'-thioxo-2'-imidazolin-2'-yl)-(Z)-2-butenoic acid (300 mg) in methanol (20 ml), a suspension of calcium carbonate (60 mg) in water (1 ml) was added, and the resultant mixture was stirred at room temperature for 2 hours. Aqueous methanol was removed by distillation, and the residue was washed with a small amount of ether and dried under reduced pressure to give 240 mg of calcium 2-methyl-3-(5'-isopropyl-5'-methyl-4'-thioxo-2'-imidazolin-2'-yl)-(Z)-2-butenoate (Compound No. 43). m.p., 160° C.-162° C.

EXAMPLE 18

2-Methyl-3-(5'-isopropyl-5'-methyl-4'-thioxo-2'-imidazolin-2'-yl)-(Z)-2-butenoic acid (300 mg) was added to aqueous ammonia (5 ml), followed by stirring at room temperature for 3 hours. After removal of excess of aqueous ammonia, the reside was dried under reduced pressure to give 320 mg of ammonium 2-methyl-3-(5'-isopropyl-5'-methyl-4'-thioxo-2'-imidazolin-2'-yl)-(Z)-2-butenoate (Compound No. 49) as a resinous material In the same manner as above, the butenoic acid derivatives (I-e) as shown in Table 8 were obtained.

TABLE 8

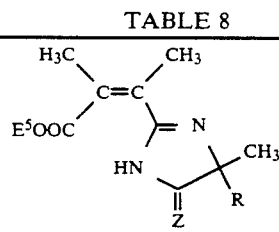
(I-e)

| Compound No. | $E^5$ | Z | R | Physical property |
|---|---|---|---|---|
| 25 | $NH_4^+$ | O | $i$-$C_3H_7$ | m.p., 110-115° C. |
| 26 | $(C_2H_5)_3N^+$ | O | $i$-$C_3H_7$ | m.p., 90-94° C. |
| 27 | O(CH_2CH_2)_2NH^+ (morpholinium) | O | $i$-$C_3H_7$ | gummy |
| 28 | cyclohexyl-NH_3^+ | O | $i$-$C_3H_7$ | gummy |
| 29 | $i$-$C_3H_7NH_3^+$ | O | $i$-$C_3H_7$ | gummy |
| 30 | $n$-$C_8H_{17}NH_3^+$ | O | $i$-$C_3H_7$ | amorphous |
| 31 | $t$-$C_4H_9NH_3^+$ | O | $i$-$C_3H_7$ | m.p., 94° C. |
| 32 | $CH_2$=$CHCH_2NH_3^+$ | O | $i$-$C_3H_7$ | gummy |
| 33 | $CH_3O(CH_2)_2NH_3^+$ | O | $i$-$C_3H_7$ | gummy |
| 34 | $Na^+$ | O | $i$-$C_3H_7$ | m.p., 136-140° C. |
| 35 | $K^+$ | O | $i$-$C_3H_7$ | m.p., 141-145° C. |
| 36 | $Li^+$ | O | $i$-$C_3H_7$ | m.p., >220° C. |
| 37 | $\frac{1}{2}Ca^{2+}$ | O | $i$-$C_3H_7$ | m.p., >230° C. |
| 38 | $\frac{1}{2}Ba^{2+}$ | O | $i$-$C_3H_7$ | m.p., >250° C. |

TABLE 8-continued

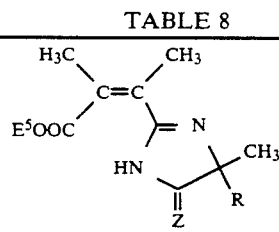
(I-e)

| Compound No. | $E^5$ | Z | R | Physical property |
|---|---|---|---|---|
| 39 | benzyl-$CH_2N(CH_3)_3^+$ | O | $i$-$C_3H_7$ | m.p., 105-107° C. |
| 40 | $CH_3(CH_2)_{15}N(CH_3)_3^+$ | O | $i$-$C_3H_7$ | m.p., 88-99° C. |
| 41 | $1/3Al^{3+}$ | O | $i$-$C_3H_7$ | m.p., 137-138° C. |
| 42 | $i$-$C_3H_7NH_3^+$ | S | $i$-$C_3H_7$ | oily |
| 43 | $\frac{1}{2}Ca^{2+}$ | S | $i$-$C_3H_7$ | m.p., 160-162° C. |
| 44 | $Na^+$ | S | $i$-$C_3H_7$ | m.p., 103-105° C. |
| 45 | $(C_2H_5)_3NH^+$ | S | $i$-$C_3H_7$ | resinous |
| 46 | $(CH_3)_3CNH_3^+$ | S | $i$-$C_3H_7$ | m.p., 97-100° C. |
| 47 | $CH_2$=$CHCH_2NH_3^+$ | S | $i$-$C_3H_7$ | resinous |
| 48 | $(CH_3CHCH_2NH_2)H^+$ with $NH_2$ | S | $i$-$C_3H_7$ | resinous |
| 49 | $NH_4^+$ | S | $i$-$C_3H_7$ | resinous |

Procedure (F)

The butenoic acid derivative (I) wherein X is either one of the following groups:

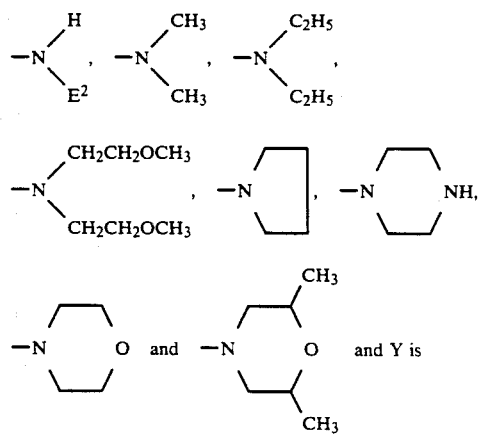

and Y is a group of the formula:

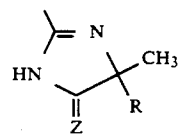

wherein $E^2$, R and Z are each as defined above, i.e. the butenoic acid derivative of the formula:

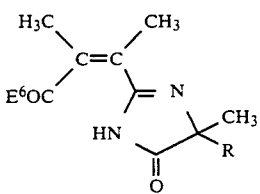 (I-f)

wherein R is as defined above and $E^6$ is either one of the following groups:

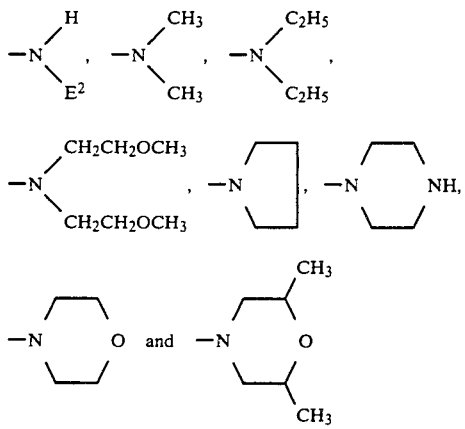

can be prepared by reacting the butenoic acid derivative of the formula:

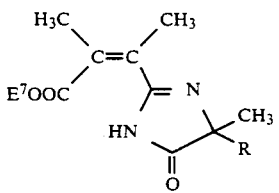 (I-b')

wherein R is as defined above and $E^7$ is a $C_1$–$C_{12}$ alkyl group with an amine of the formula:

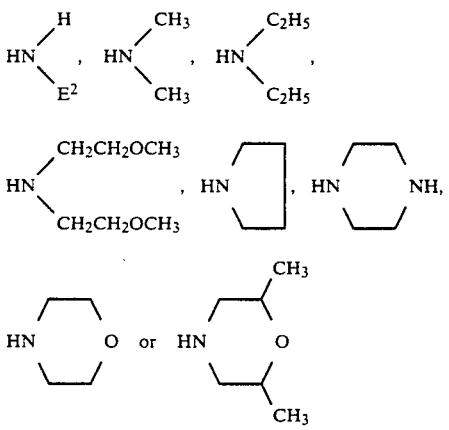

wherein $E^2$ is as defined above.

The reaction is performed usually in the presence or absence of a solvent at a temperature of about 0° C. to 100° C. for a period of about 30 minutes to 6 hours. The amine is used in an amount of about 1 equivalent or more to 1 equivalent of the butenoic acid derivative (I-b'). Examples of the solvent are halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethyleneglycol dimethyl ether), alcohols (e.g. methanol, ethanol, isopropanol, t-butanol), or their mixtures.

Post treatment of the reaction mixture may be effected by a per se conventional procedure. For instance, the solvent is removed from the reaction mixture, and the residue is crystallized from a suitable solvent system such as a mixture of hexane and acetone or a mixture of hexane and ether, followed by filtration. The collected crystals may be, if necessary, washed with an appropriate solvent such as ether. Chromatography, recrystallization or any other purification may be also applied thereto.

In the same manner as above, the butenoic acid derivatives (I-f) as shown in Table 9 are obtainable.

TABLE 9

(I-f) structure shown

| $E^6$ | R |
|---|---|
| —NHCH₃ | C₂H₅ |
| —NHCH₃ | i-C₃H₇ |
| —NHCH₃ | —CH(CH₂)(CH₂) (cyclopropyl) |
| —NHC₂H₅ | C₂H₅ |
| —NHC₂H₅ | i-C₃H₇ |
| —NHC₂5 | —CH(CH₂)(CH₂) (cyclopropyl) |
| —NHC₃H₇(n) | C₂H₅ |
| —NHC₃H₇(n) | i-C₃H₇ |
| —NHC₃H₇(n) | —CH(CH₂)(CH₂) (cyclopropyl) |
| —NHC₃H₇(i) | C₂H₅ |
| —NHC₃H₇(i) | i-C₃H₇ |
| —NHC₃H₇(i) | —CH(CH₂)(CH₂) (cyclopropyl) |
| —NHC₄H₉(n) | C₂H₅ |
| —NHC₄H₉(n) | i-C₃H₇ |
| —NHC₄H₉(n) | —CH(CH₂)(CH₂) (cyclopropyl) |
| —NHC₄H₉(i) | C₂H₅ |
| —NHC₄H₉(i) | i-C₃H₇ |

TABLE 9-continued

Structure (I-f):

$H_3C$, $CH_3$ on $C=C$; $E^6OC(=O)$ group; connected to $C=N$; HN-C(=O)-C(CH_3)(R)-

| $E^6$ | R |
|---|---|
| $-NHC_4H_9(i)$ | $-CH(CH_2CH_2)$ (cyclopropyl) |
| $-NHC_4H_9(t)$ | $C_2H_5$ |
| $-NHC_4H_9(t)$ | $i-C_3H_7$ |
| $-NHC_4H_9(t)$ | $-CH(CH_2CH_2)$ (cyclopropyl) |
| $-NHC_4H_9(sec)$ | $C_2H_5$ |
| $-NHC_4H_9(sec)$ | $i-C_3H_7$ |
| $-NHC_4H_9(sec)$ | $-CH(CH_2CH_2)$ (cyclopropyl) |
| $-NHC_5H_{11}(n)$ | $C_2H_5$ |
| $-NHC_5H_{11}(n)$ | $i-C_3H_7$ |
| $-NHC_5H_{11}(n)$ | $-CH(CH_2CH_2)$ (cyclopropyl) |
| $-NHC_6H_{13}(n)$ | $C_2H_5$ |
| $-NHC_6H_{13}(n)$ | $i-C_3H_7$ |
| $-NHC_6H_{13}(n)$ | $-CH(CH_2CH_2)$ (cyclopropyl) |
| $-NHC_7H_{15}(n)$ | $C_2H_5$ |
| $-NHC_7H_{15}(n)$ | $i-C_3H_7$ |
| $-NHC_7H_{15}(n)$ | $-CH(CH_2CH_2)$ (cyclopropyl) |
| $-NHC_8H_{17}(n)$ | $C_2H_5$ |
| $-NHC_8H_{17}(n)$ | $i-C_3H_7$ |
| $-NHC_8H_{17}(n)$ | $-CH(CH_2CH_2)$ (cyclopropyl) |
| $-NHC_9H_{19}(n)$ | $C_2H_5$ |
| $-NHC_9H_{19}(n)$ | $i-C_3H_7$ |
| $-NHC_9H_{19}(n)$ | $-CH(CH_2CH_2)$ (cyclopropyl) |
| $-NHC_{10}H_{21}(n)$ | $C_2H_5$ |
| $-NHC_{10}H_{21}(n)$ | $i-C_3H_7$ |
| $-NHC_{10}H_{21}(n)$ | $-CH(CH_2CH_2)$ (cyclopropyl) |
| $-NHC_{11}H_{23}(n)$ | $C_2H_5$ |
| $-NHC_{11}H_{23}(n)$ | $i-C_3H_7$ |
| $-NHC_{11}H_{23}(n)$ | $-CH(CH_2CH_2)$ (cyclopropyl) |
| $-NHOH$ | $C_2H_5$ |
| $-NHOH$ | $i-C_3H_7$ |
| $-NHOH$ | $-CH(CH_2CH_2)$ (cyclopropyl) |
| $-NHCH(CH_2CH_2)$ (cyclopropyl-N) | $C_2H_5$ |
| $-NHCH(CH_2CH_2)$ (cyclopropyl-N) | $i-C_3H_7$ |
| $-NHCH(CH_2CH_2)$ (cyclopropyl-N) | $-CH(CH_2CH_2)$ (cyclopropyl) |
| $-NHCH(CH_2CH_2CH_2CH_2)$ (cyclopentyl-N) | $C_2H_5$ |
| $-NHCH(CH_2CH_2CH_2CH_2)$ (cyclopentyl-N) | $i-C_3H_7$ |
| $-NHCH(CH_2CH_2CH_2CH_2)$ (cyclopentyl-N) | $-CH(CH_2CH_2)$ (cyclopropyl) |
| $-NHCH(CH_2CH_2CH_2CH_2CH_2)$ (cyclohexyl-N) | $C_2H_5$ |

TABLE 9-continued $$\text{(I-f)}\quad \underset{\underset{R}{|}}{\underset{HN}{\overset{O}{\|}}}\underset{CH_3}{\overset{H_3C\ \ CH_3}{\underset{E^6OC}{\overset{\diagdown\ \ /}{C=C}}}}\underset{CH_3}{\overset{N}{\diagdown}}$$

| $E^6$ | R |
|---|---|
| —NHCH(CH₂CH₂)₂CH₂ (cyclohexyl) | i-C₃H₇ |
| —NHCH(CH₂CH₂)₂CH₂ (cyclohexyl) | —CH(CH₂)₂ (cyclopropyl) |
| —NHCH₂CH₂OCH₃ | C₂H₅ |
| —NHCH₂CH₂OCH₃ | i-C₃H₇ |
| —NHCH₂CH₂OCH₃ | —CH(CH₂)₂ |
| —NHCH₂CH₂OH | C₂H₅ |
| —NHCH₂CH₂OH | i-C₃H₇ |
| —NHCH₂CH₂OH | —CH(CH₂)₂ |
| —NHCH(CH₃)CH₂CN | C₂H₅ |
| —NHCH(CH₃)CH₂CN | i-C₃H₇ |
| —NHCH(CH₃)CH₂CN | —CH(CH₂)₂ |
| —NHCH₂CH=CH₂ | C₂H₅ |
| —NHCH₂CH=CH₂ | i-C₃H₇ |
| —NHCH₂CH=CH₂ | —CH(CH₂)₂ |
| —NHC(CH₃)₂C≡CH | C₂H₅ |
| —NHC(CH₃)₂C≡CH | i-C₃H₇ |
| —NHC(CH₃)₂C≡CH | —CH(CH₂)₂ |
| —NHCH₂C≡CH | C₂H₅ |
| —NHCH₂C≡CH | i-C₃H₇ |
| —NHCH₂C≡CH | —CH(CH₂)₂ |
| —NHCH₂C(O)NH₂ | C₂H₅ |
| —NHCH₂C(O)NH₂ | i-C₃H₇ |
| —NHCH₂C(O)NH₂ | —CH(CH₂)₂ |
| —NHCH₂C₆H₅ | C₂H₅ |
| —NHCH₂C₆H₅ | i-C₃H₇ |
| —NHCH₂C₆H₅ | —CH(CH₂)₂ |
| —NHCH₂CH₂C₆H₅ | C₂H₅ |
| —NHCH₂CH₂C₆H₅ | i-C₃H₇ |
| —NHCH₂CH₂C₆H₅ | —CH(CH₂)₂ |
| —NH(CH₂)₃C₆H₅ | C₂H₅ |

TABLE 9-continued $$\underset{\underset{O}{\overset{HN}{\|}}}{\overset{H_3C}{\underset{E^6OC}{\succ}}}\overset{CH_3}{\underset{\underset{R}{\overset{CH_3}{\succ}}}{\overset{N}{\|}}}$$  (I-f)

| $E^6$ | R |
|---|---|
| —NH(CH₂)₃—C₆H₅ | i-C₃H₇ |
| —NH(CH₂)₃—C₆H₅ | —CH(CH₂CH₂) (cyclopropyl) |
| —NHCH(CH₃)—C₆H₅ | C₂H₅ |
| —NHCH(CH₃)—C₆H₅ | i-C₃H₇ |
| —NHCH(CH₃)—C₆H₅ | —CH(CH₂CH₂) (cyclopropyl) |
| —NHCH(CH₃)COOC₂H₅ | C₂H₅ |
| —NHCH(CH₃)COOC₂H₅ | i-C₃H₇ |
| —NHCH(CH₃)COOC₂H₅ | —CH(CH₂CH₂) (cyclopropyl) |
| —NHCH₂-(tetrahydrofuran-2-yl) | C₂H₅ |
| —NHCH₂-(tetrahydrofuran-2-yl) | i-C₃H₇ |
| —NHCH₂-(tetrahydrofuran-2-yl) | —CH(CH₂CH₂) (cyclopropyl) |
| —N(CH₃)₂ | C₂H₅ |
| —N(CH₃)₂ | i-C₃H₇ |
| —N(CH₃)₂ | —CH(CH₂CH₂) (cyclopropyl) |
| —N(C₂H₅)₂ | C₂H₅ |
| —N(C₂H₅)₂ | i-C₃H₇ |
| —N(C₂H₅)₂ | —CH(CH₂CH₂) (cyclopropyl) |
| —N(pyrrolidin-1-yl) | C₂H₅ |
| —N(pyrrolidin-1-yl) | i-C₃H₇ |
| —N(pyrrolidin-1-yl) | —CH(CH₂CH₂) (cyclopropyl) |
| —N(piperazin-1-yl)NH | C₂H₅ |
| —N(piperazin-1-yl)NH | i-C₃H₇ |
| —N(piperazin-1-yl)NH | —CH(CH₂CH₂) (cyclopropyl) |
| —N(morpholin-4-yl) | C₂H₅ |

TABLE 9-continued $$\underset{\underset{O}{\overset{\|}{C}}-\underset{R}{\overset{CH_3}{C}}-CH_3}{\underset{HN}{\overset{E^6OC}{\diagdown}}\overset{H_3C}{\underset{}{C=C}}\overset{CH_3}{\diagup}\overset{}{\diagdown}N}$$
(I-f)

| E⁶ | R |
|---|---|
| −N(−CH₂CH₂−)₂O (morpholino) | i-C₃H₇ |
| −N(−CH₂CH₂−)₂O (morpholino) | −CH(CH₂)₂ (cyclopropyl) |
| −N(−CH(CH₃)CH₂−)O (2-methylmorpholino) | C₂H₅ |
| −N(−CH(CH₃)CH₂−)O (2-methylmorpholino) | i-C₃H₇ |
| −N(−CH(CH₃)CH₂−)O (2-methylmorpholino) | −CH(CH₂)₂ |
| −NH₂ | C₂H₅ |
| −NH₂ | i-C₃H₇ |
| −NH₂ | −CH(CH₂)₂ |

Some practical embodiments for production of the butenoic acid derivatives (I-f) are as follows:

EXAMPLE 19

Ethyl 2-methyl-3-(5'-isopropyl-5'-methyl-4'-oxo-2'-imidazolin-2'-yl)-(Z)-2-butenoate (700 mg) was added to t-butylamine (5 ml), followed by stirring at room temperature for 1 hour. The reaction mixture was filtered through a glass filter to collect a solid material, which was thoroughly washed with ether (5 ml) and dried to give 640 mg of N-t-butyl-2-methyl-3-(5'-isopropyl-5'-methyl-4'-oxo-2'-imidazolin-2'-yl)-(Z)-2-butenoic acid amide (Compound No. 54) m.p., 176° C.–178° C.

EXAMPLE 20

Ethyl 2-methyl-3-(5'-isopropyl-5'-methyl-4'-oxo-2'-imidazolin-2'-yl)-(Z)-2-butenoate (700 mg) was added to 30% aqueous ammonia (20 ml), followed by stirring at room temperature for 4 hours. The crystals were collected by filtration and dried to give 240 mg of 2-methyl-3-(5'-isopropyl-5'-methyl-4'-oxo-2' imidazolin-2'-yl)-(Z)-2-butenoic acid amide (Compound No. 55). m.p., 201° C.–203° C.

In the same manner as above, the butenoic acid derivatives (I-f) as shown in Table 9 were obtained.

TABLE 9

$$\underset{\underset{O}{\overset{\|}{C}}-\underset{R}{\overset{CH_3}{C}}-CH_3}{\underset{HN}{\overset{E^6OC}{\diagdown}}\overset{H_3C}{\underset{}{C=C}}\overset{CH_3}{\diagup}\overset{}{\diagdown}N}$$
(I-f)

| Compound No. | E⁶ | R | Physical property |
|---|---|---|---|
| 50 | −NHCH₃ | i-C₃H₇ | m.p., 190–192° C. |
| 51 | −N(CH₃)₂ | i-C₃H₇ | m.p., 146–148° C. |
| 52 | −N(C₂H₅)₂ | i-C₃H₇ | m.p., 133–134° C. |
| 53 | −NHC₃H₇(i) | i-C₃H₇ | m.p., 182–183° C. |
| 54 | −NHC₄H₉(t) | i-C₃H₇ | m.p., 176–178° C. |
| 55 | −NH₂ | i-C₃H₇ | m.p., 201–203° C. |
| 56 | −NHC₅H₁₁(n) | i-C₃H₇ | m.p., 166–168° C. |
| 57 | −NHC(CH₃)₂−C≡CH | i-C₃H₇ | m.p., 170–172° C. |
| 58 | −NHCH₂−C₆H₅ | i-C₃H₇ | m.p., 185–187° C. |
| 59 | −NHCH₂CH₂OH | i-C₃H₇ | m.p., 113–116° C. |
| 60 | −NHCH₂CH₂−C₆H₅ | i-C₃H₇ | m.p., 184–186° C. |
| 61 | −NHC₄H₉(i) | i-C₃H₇ | m.p., 184–185° C. |
| 62 | −NHC₄H₉(sec) | i-C₃H₇ | m.p., 158–160° C. |
| 63 | −NHCH(CH₃)−C₆H₅ | i-C₃H₇ | m.p., 149–151° C. |
| 64 | −NHCH₂−(tetrahydrofuran-2-yl) | i-C₃H₇ | m.p., 170–171° C. |
| 65 | −NH−(pyrrolidin-1-yl, H) | i-C₃H₇ | m.p., >205° C. (decomp.) |

TABLE 9-continued (I-f)

$$\underset{\underset{\underset{O}{\overset{\|}{C}}}{\overset{|}{\underset{HN}{\overset{}{}}}}{\overset{}{}}}{\overset{H_3C}{\underset{E^6OC}{\overset{}{C}}}=\overset{CH_3}{\underset{}{C}}-N=\underset{R}{\overset{CH_3}{\underset{}{C}}}}$$

| Compound No. | $E^6$ | R | Physical property |
|---|---|---|---|
| 66 | —NHCH(CH₃)CH₂CN | i-C₃H₇ | m.p., 103–104° C. |
| 67 | —NHCH(CH₃)COOC₂H₅ | i-C₃H₇ | resinous |
| 68 | —NHCH₂C(=O)NH₂ | i-C₃H₇ | m.p., 134–136° C. |
| 69 | —NHC₄H₉(n) | i-C₃H₇ | m.p., 184–186° C. |
| 70 | —NHCH₂CH=CH₂ | i-C₃H₇ | m.p., 153–155° C. |
| 71 | —NHCH₂C≡CH | i-C₃H₇ | m.p., 168–170° C. |
| 72 | —N(CH₂CH₂OCH₃)₂ | i-C₃H₇ | $n_D^{17.5}$ 1.5079 |
| 73 | —NHC₂H₅ | i-C₃H₇ | m.p., 180–182° C. |
| 74 | —NH(CH₂)₁₀CH₃ | i-C₃H₇ | m.p., 135–137° C. |
| 75 | —N(morpholino) | i-C₃H₇ | m.p., 118–120° C. |
| 76 | —NH-cyclohexyl | i-C₃H₇ | m.p., 156–160° C. |
| 77 | —NH(CH₂)₃-phenyl | i-C₃H₇ | resinous |
| 78 | —N(2,6-dimethylmorpholino) | i-C₃H₇ | $n_D^{17.5}$ 1.4971 |
| 79 | —N(pyrrolidino) | i-C₃H₇ | $n_D^{17.5}$ 1.4432 |
| 80 | —NHOH | i-C₃H₇ | resinous |

Procedure (G)

The butenoic acid derivative (I) wherein X is a hydroxyl group and Y is a group of the formula:

$$\underset{\underset{Z}{\overset{\|}{}}}{\overset{H}{\underset{HN}{\overset{}{\underset{}{N}}}}}\underset{R}{\overset{CH_3}{\underset{}{C}}}$$

wherein R and Z are each defined above or its salt, i.e. the butenoic acid derivative of the formula:

$$\underset{\underset{Z}{\overset{\|}{}}}{\overset{H_3C}{\underset{HOOC}{\overset{}{C}}}=\overset{CH_3}{\underset{}{C}}\underset{HN}{\overset{H}{\underset{}{N}}}\underset{R}{\overset{CH_3}{\underset{}{C}}}}$$ (I-g)

wherein R and Z are each as defined above or its salt, can be produced by reacting the butenoic acid derivative (I-c) with sodium cyanoborohydride in a solvent under an acidic condition.

The reaction is accomplished at a temperature of from about 0° C. to 50° C., preferably from about 0° C. to room temperature, for a period of about 10 minutes to 5 hours. Sodium cyanoborohydride is normally employed in an amount of about 1 equivalent or more, preferably of about 1 to 2 equivalents, to 1 equivalent of the butenoic acid derivative (I-c). In order to conduct the reaction in an acidic condition, hydrochloric acid, sulfuric acid or the like may be introduced into the reaction system. Further, the reaction is preferably carried out in a nitrogen atmosphere. Examples of the solvent are lower alcohols (e.g. methanol, ethanol), etc.

After completion of the reaction, the reaction mixture may be adjusted to pH 1 with an acid such as hydrochloric acid, and then an alkali such as an aqueous solution of sodium hydrogencarbonate is added thereto so as to make a pH of about 2 to 3. The resulting mixture is poured into water and extracted with an organic solvent, followed by concentration of the extract. Alternatively, the reaction mixture may be concentrated, and the residue is extracted with an organic solvent (e.g. methanol). After removal of the produced inorganic salt by filtration, the filtrate is concentrated. When desired, any purification procedure such as chromatography or recrystallization may be applied to the resultant product.

As the salt of the butenoic acid derivative (I-g), there are exemplified hydrochloride, hydrobromide, etc. Such salt may be produced by introducing hydrogen chloride gas or hydrogen bromide gas into a solution of the butenoic acid derivative (I-g) in a suitable solvent. Usually, this salt formation reaction is carried out at a temperature of about 0° C. to 50° C. for a period of about 0.5 to 5 hours. The hydrogen chloride gas or hydrogen bromide gas may be used in an amount of about 1 equivalent or more to 1 equivalent of the butenoic acid derivative (I-g). Examples of the solvent are halogenated hydrocarbons (e.g. methylene chloride, chlorobenzene, dichlorobenzene), ethers (e.g. diethyl ether, dioxane, tetrahydrofuran), etc.

Post treatment of the reaction mixture may be carried out by a per se conventional procedure. For instance, the reaction mixture is subjected to filtration, whereby the precipitated crystals are collected. When desired, the collected crystals may be purified, for instance, by recrystallization.

In the same manner as above, the butenoic acid derivatives (I-g) or their salts as shown in Table 10 are obtainable.

TABLE 10

$$\underset{HOOC}{\overset{H_3C}{>}}C=C\underset{\underset{Z}{\overset{\|}{HN}}\underset{R}{\overset{CH_3}{<}}}{\overset{H}{<}}NH$$ (I-g)

| Z | R | Form of salt |
|---|---|---|
| O | $C_2H_5$ | Free |
| O | $C_2H_5$ | Hydrochloride |
| O | $C_2H_5$ | Hydrobromide |
| O | $i\text{-}C_3H_7$ | Free |
| O | $i\text{-}C_3H_7$ | Hydrochloride |
| O | $i\text{-}C_3H_7$ | Hydrobromide |
| O | $-CH\overset{CH_2}{\underset{CH_2}{<}}$ | Free |
| O | $-CH\overset{CH_2}{\underset{CH_2}{<}}$ | Hydrochloride |
| O | $-CH\overset{CH_2}{\underset{CH_2}{<}}$ | Hydrobromide |
| S | $C_2H_5$ | Free |
| S | $C_2H_5$ | Hydrochloride |
| S | $C_2H_5$ | Hydrobromide |
| S | $i\text{-}C_3H_7$ | Free |
| S | $i\text{-}C_3H_7$ | Hydrochloride |
| S | $i\text{-}C_3H_7$ | Hydrobromide |
| S | $-CH\overset{CH_2}{\underset{CH_2}{<}}$ | Free |
| S | $-CH\overset{CH_2}{\underset{CH_2}{<}}$ | Hydrochloride |
| S | $-CH\overset{CH_2}{\underset{CH_2}{<}}$ | Hydrobromide |

Some practical embodiments for production of the butenoic acid derivatives (I-g) are as follows:

EXAMPLE 21

To a solution of 2-methyl-3-(5'-isopropyl-5'-methyl-4'-oxo-2'-imidazolin-2'-yl)-(Z)-2-butenoic acid (1.0 g) in methanol (50 ml), a methanolic solution of 2N hydrochloric acid was added to make a pH of 2 to 3. Under nitrogen atmosphere, sodium cyanoborohydride (300 mg) was added thereto, followed by stirring at room temperature for 30 minutes, during which a methanolic solution of 2N hydrochloric acid was portionwise added thereto to keep the reaction mixture at a pH of 2 to 3. Stirring was continued at the same temperature for 1 hour. After completion of the reaction, conc. hydrochloric acid was added thereto to make a pH of 1, and an aqueous solution of sodium hydrogencarbonate was added thereto to adjust at pH 2–3. The resultant mixture was poured into water, extracted with chloroform, dried over anhydrous magnesium sulfate and concentrated to give 340 mg of 2-methyl-3-(5'-isopropyl-5'-methyl-4'-oxo-imidazolidin-2'-yl)-(Z)-2-butenoic acid (Compound No. 81 (trans)). m.p., 174° C.–176° C.

NMR ≃ (CDCl$_3$) (ppm): 0.8–1.0 (6H, m), 1.45 (3H, s), 1.8–2.0 (6H, m).

EXAMPLE 22

To a solution of 2-methyl-3-(5'-isopropyl-5'-methyl-4'-oxo-2'-imidazolin-2'-yl)-(Z)-2-butenoic acid (2.0 g) in methanol (80 ml), a methanolic solution of 2N hydrochloric acid was added to make a pH of 2 to 3. Under nitrogen atmosphere, sodium cyanoborohydride (530 mg) was added thereto, followed by stirring at room temperature for 30 minutes, during which a methanolic solution of 2N hydrochloric acid was portionwise added thereto to keep the reaction mixture at a pH of 2 to 3. Additional 530 mg of sodium cyanoborohydride were added thereto, and stirring was continued for 30 minutes while controlling the pH. The above operation was repeated twice, and then stirring was continued at room temperature for 1 hour. After completion of the reaction, conc. hydrochloric acid was added thereto to make a pH of 1, and an aqueous solution of sodium hydrogencarbonate was added thereto to adjust at pH 2–3. The resultant mixture was concentrated under reduced pressure. To the residue, methanol (50 ml) was added, and the insoluble salt as separated was eliminated by filtration. The filtrate was concentrated to give a mixture of the cis and trans isomers of 2-methyl-3-(5'-isopropyl-5'-methyl-4'-oxo-imidazolidin-2'-yl)-(Z)-2-butenoic acid (Compound No. 81). Purification of the mixture by silica gel column chromatography using hexane-acetone and methanol as the eluting agents gave the trans isomer (200 mg) as the first eluting fraction and the cis isomer (180 mg) as the second eluting fraction.

Trans isomer (Compound No. 81 (trans)), m.p., 174° C.–176° C. NMR 6 (CDCl$_3$) (ppm): 0.8–1.0 (6H, m), 1.45 (3H, s), 1.8–2.0 (6H, m).

Cis isomer (Compound No. 81 (cis)), m.p., 55° C.–57° C. NMR (CDCl$_3$) (ppm): 0.6–1.6 (15H, m).

EXAMPLE 23

To a solution of 2-methyl-3-(5'-isopropyl-5'-methyl-4'-thioxo-2'-imidazolin-2'-yl)-(Z)-2-butenoic acid (1.0 g) in methanol (50 ml), a methanolic solution of 2N hydrochloric acid was added to make a pH of 2 to 3. Under nitrogen atmosphere, sodium cyanoborohydride (300 mg) was added thereto, followed by stirring at room temperature for 30 minutes, during which a methanolic solution of 2N hydrochloric acid was portionwise added thereto to keep the reaction mixture at pH 2–3. Stirring was continued at the same temperature for 1 hour. Sodium cyanoborohydride (300 mg) was further added thereto to keep the mixture at pH 2–3, followed by stirring for 1 hour. After completion of the reaction, conc. hydrochloric acid was added thereto to make the reaction mixture at pH 1, and an aqueous solution of sodium hydrogencarbonate was added thereto to adjust at pH 2–3. The resultant mixture was poured into water, extracted with chloroform, dried over anhydrous magnesium sulfate and concentrated to give a mixture of the cis and trans isomers of 2-methyl-3-(5'-isopropyl-5'-methyl-4'-thioxoimidazolidin-2'-yl)-(Z)-2-butenoic acid (Compound No. 82) as an oil. The oil was purified by silica gel column chromatography using a mixture of hexane and acetone as the eluting agent to give the trans isomer (100 mg) as the first eluting fraction and the cis isomer (110 mg) as the second eluting fraction.

Trans isomer (Compound No. 82 (trans)), $n_D^{27.0}$ 1.5650. NMR δ (CDCl$_3$) (ppm): 0.6–1.1 (6H, m), 1.38 (3H, s), 1.7–1.9 (6H, m).

Cis isomer (Compound No. 82 (cis)), m.p., 95° C.–97° C. NMR δ (CDCl$_3$) (ppm): 0.7–1.4 (15H, m).

Production of the intermediary compounds (II), (III), (IV) are further explained in detail below.

The compound (II), i.e. the dioxopyrroline compound of the formula:

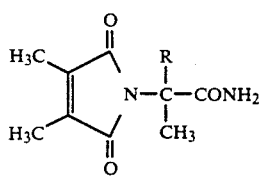
(II)

wherein R is as defined above, can be prepared by (1) reacting an aminonitrile [U.S. Pat. No. 4,062,671] of the formula:

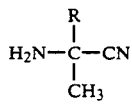
(VI)

wherein R is as defined above with 2,3-dimethylmaleic anhydride of the formula:

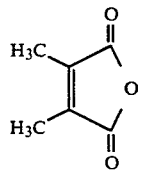

in the presence of a tertiary amine to give a maleic acid amine salt of the formula:

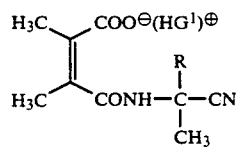
(VII)

wherein R is as defined above and G$^1$ is a tertiary amine, (2) reacting the thus obtained maleic acid amine salt (VII) with a dehydrating agent to give a dioxopyrrolinenitrile of the formula:

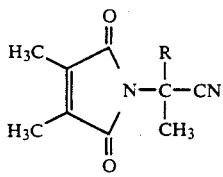
(VIII)

wherein R is as defined above and (3) hydrolyzing the dioxopyrrolinenitrile (VII) with an acid.

The reaction at the step (1) is normally carried out in the presence or absence of a solvent at a temperature of about 0° C. to 120° C. for a period of about 1 to 24 hours. The 2,3-dimethylmaleic acid anhydride and the tertiary amine may be used respectively in amounts of about 0.5 to 1 equivalent and of 1 equivalent or more (preferably 1 to 1.5 equivalents) to 1 equivalent of the aminonitrile (VI). Examples of the solvent are aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethyleneglycol dimethyl ether), ketones (e.g. acetone, methylethylketone, methylisobutylketone, cyclohexanone), esters (e.g. ethyl formate, ethyl acetate, butyl acetate, diethyl carbonate), nitriles (e.g. acetonitrile, isobutylonitrile), tertiary amines (e.g. pyridine, triethylamine, N,N-diethylaniline, tributylamine, N-methylmorpholine), and their mixtures. As the tertiary amine, there may be used, for instance, triethylamine, diisopropylethylamine, tributylamine, 1,4-diazabicyclo-[2.2.0]octane (Dabco), 1,8-diazabicyclo [5.4.0]undeca-7-ene (DBU), etc.

Post treatment of the reaction mixture may be carried out, for instance, by evaporation of the solvent or precipitating the amine salt. The collected product may be, if necessary, further purified by recrystallization or the like.

The reaction at the step (2) may be effected in the presence or absence of a solvent at a temperature of about −10° C. to 130° C. for a period of about 10 minutes to 2 hours. The dehydrating agent is used normally in an amount of about 2 equivalents or more to 1 equivalent of the maleic acid amine salt (VII). As the solvent, there may be used, for instance, aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethyleneglycol dimethyl ether), nitriles (e.g. acetonitrile, isobutylonitrile), tertiary amines (e.g. pyridine, triethylamine, N,N-diethylaniline, tributylamine, N-methylmorpholine) or their mixtures. Examples of the dehydrating agent are thionyl chloride, phosphorus oxychloride, acetic anhydride, trifluoroacetic anhydride, etc.

Post treatment of the reaction mixture may be performed by a per se conventional procedure depending upon the kind of the dehydrating agent as used. When thionyl chloride or phosphorus oxychloride is used, the reaction mixture may be poured into ice-water, followed by extraction with an organic solvent. When using the solvent and acetic anhydride or trifluoroacetic anhydride, the reaction mixture may be concentrated under reduced pressure, optionally followed by purification such as recrystallization and chromatography.

The reaction at the step (3) is ordinarily carried out in the presence or absence of a solvent at a temperature of about 0° C. to 50° C. for a period of about 0.5 to 24 hours. The acid may be used in an amount of 1 equivalent or more, preferably of about 2 to 3 equivalents, to 1 equivalent of the dioxopyrrolinenitrile (VIII). As the solvent, there may be used, for instance, halogenated hydrocarbons (e.g. methylene chloride, chloroform, carbon tetrachloride, dichloroethane). Examples of the acid are conc. sulfuric acid, conc. hydrochloric acid, etc.

The reaction mixture may be poured into water and extracted with an organic solvent, followed by concentration. When desired, the resultant product may be purified by chromatography, distillation or recrystallization.

In the manner as illustrated above, the dioxopyrrolinenitriles (VIII) and the dioxopyrroline compounds (II) as shown in Tables 11 and 12 are obtainable.

TABLE 11

(VIII)

| R | Physical property |
|---|---|
| $C_2H_5$ | $n_D^{26.0}$ 1.4803 |
| $i-C_3H_7$ | $n_D^{26.5}$ 1.4840 |
| $-CH\begin{matrix}CH_2\\CH_2\end{matrix}$ | $n_D^{26.0}$ 1.4818 |

TABLE 12

(II)

| R | Physical property |
|---|---|
| $C_2H_5$ | m.p., 110–112° C. |
| $i-C_3H_7$ | m.p., 124–126° C. |
| $-CH\begin{matrix}CH_2\\CH_2\end{matrix}$ | m.p., 144–146° C. |

Some practical embodiments for production of the dioxopyrroline compound (II) are shown below.

EXAMPLE 24

Dioxopyrrolinenitrile (VIII)

To a solution of 2,3-dimethylmaleic anhydride (4.0 g) in tetrahydrofuran (50 ml), 2-amino-2,3-dimethyl-butyronitrile (3.6 g) and triethylamine (3.5 g) were added, and the resultant mixture was stirred at room temperature for 2 hours. After removal of tetrahydrofuran, acetic anhydride (20 ml) was added thereto, and heating under reflux was effected for 2 hours. Excess of acetic anhydride and acetic acid were removed, and the residue was dissolved in methylene chloride, washed with water and dried over anhydrous magnesium sulfate. After removal of the magnesium sulfate by filtration, the filtrate was concentrated, and the resultant oily product was purified by silica gel column chromatography to give 3.0 g of alpha-isopropyl-alpha-methyl-(2,5-dioxo-3,4-dimethyl-3-pyrroline)-1-acetonitrile. $n_D^{26.5}$ 1.4840. Yield, 42%.

EXAMPLE 25

Dioxopyrroline compound (II)

To a solution of alpha-isopropyl-alpha-methyl-(2,5-dioxo-3,4-dimethyl-3-pyrroline)-1-acetonitrile (3.0 g) in methylene chloride (30 ml), conc. sulfuric acid (3 ml) was dropwise added in 1 hour, during which the temperature was kept between room temperature and 35° C. The resultant mixture was stirred at room temperature for 2 hours and then poured into water. The resulting mixture was extracted with chloroform. The extract was washed with a sodium bicarbonate solution, dried over anhydrous magnesium sulfate and concentrated. The residue was washed with ether to give 1.82 g of alpha-isopropyl-alpha-methyl-(2,5-dioxo-3,4-di-methyl-3-pyrroline)-1-acetamide. m.p., 124° C.–126° C. Yield, 56%.

The compound (III), i.e. the maleamide compound of the formula:

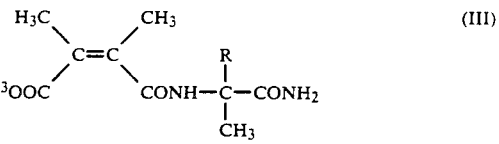

(III)

wherein R and $E^3$ are each as defined above, can be prepared by reacting (1) an amino-amide [cf. U.S. Pat. No. 4,062,671] of the formula:

(IX)

wherein R and Z are each as defined above with 2,3-dimethylmaleic anhydride of the formula:

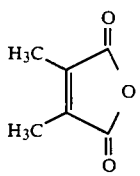

in the presence of a tertiary amine to give a maleamide amine salt of the formula:

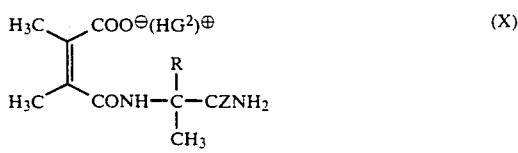

(X)

wherein R and Z are each as defined above and $G^2$ is a tertiary amine and (2) reacting the maleamide amine salt (X) wherein Z is an oxygen atom with a halogen compound of the formula:

$$E^3\text{-}A \quad (XI)$$

wherein $E^3$ is as defined above and A is a halogen atom (e.g. chlorine, bromine, iodine).

The reaction at the step (1) is normally carried out in a solvent at a temperature of about 0° C. to 130° C. for a period of about 0.5 to 24 hours. The 2,3-dimethylmaleic acid anhydride and the tertiary amine are respectively used in amounts of about 0.5 to 1 equivalent and of about 1 to 5 equivalents (preferably 1 to 1.5 equivalents) to 1 equivalent of the amino-amide (IX). Examples of the solvent are aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethyleneglycol dimethyl ether), ketones (e.g. acetone, methylethylketone, methylisobutylketone, cyclohexanone), esters (e.g. ethyl formate, ethyl acetate, butyl acetate, diethylcarbonate), nitriles (e.g. acetonitrile, isobutylonitrile), tertiary amines (e.g. pyridine, triethylamine, N,N-diethylaniline, tributylamine, N-methylmorpholine), acid amides (e.g. formamide, N,N-dimethylformamide, acetoamide) and their mixtures. As the tertiary amine, there may be used triethylamine, tributylamine, diisopropylethylamine, 1,4-diazabicyclo[2.2.0] octane (Dabco), 1,8-diazabicyclo[5.4.0] undeca-7-ene (DBU), etc.

The reaction mixture may be subjected to a post treatment by a per se conventional procedure. For instance, the solvent is removed from the reaction mixture by distillation or the precipitated amine salt is collected by filtration. When desired, the resulting product may be purified by recrystallization or the like.

The reaction at the step (2) is usually carried out in a solvent at a temperature of about 0° C. to 120° C. for a period of about 2 to 24 hours. The halogenated compound (XI) may be employed in an amount of 1 to 5 equivalents to 1 equivalent of the maleamide amine salt (X) wherein Z is an oxygen atom. Examples of the solvent are (e.g. acetone, methylethylketone, methylisobutylketone, isophorone, cyclohexanone), esters (e.g. ethyl formate, ethyl acetate, butyl acetate, diethylcarbonate), nitriles (e.g. acetonitrile, isobutylonitrile), tertiary amines (e.g. pyridine, triethylamine, N,N-diethylaniline, tributylamine, N-methylmorpholine), acid amides (e.g. formamide, N,N-dimethylformamide, acetoamide) and their mixtures.

Post treatment of the reaction mixture may be effected, for instance, by pouring it into water and extracting the resultant mixture with an organic solvent, optionally followed by concentration. If necessary, the resultant product may be purified by chromatography, recrystallization or the like.

In the manner as illustrated above, the maleamide amine salts (X) and the maleamide compounds (III) as shown in Tables 13 and 14 are obtainable.

TABLE 13

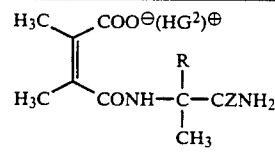
(X)

| R | Z | $G^2$ |
|---|---|---|
| $C_2H_5$ | O | $N(CH_3)_3$ |
| $i$-$C_3H_7$ | O | $N(CH_3)_3$ |
| —CH(CH₂)₂ (cyclopropyl) | O | $N(CH_3)_3$ |
| $C_2H_5$ | S | $N(CH_3)_3$ |
| $i$-$C_3H_7$ | S | $N(CH_3)_3$ |
| —CH(CH₂)₂ (cyclopropyl) | S | $N(CH_3)_3$ |

TABLE 14

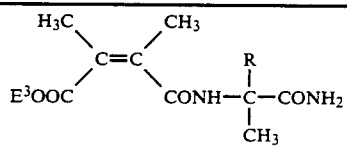
(III)

| $E^3$ | R |
|---|---|
| $CH_3$ | $C_2H_5$ |
| $CH_3$ | $i$-$C_3H_7$ |
| $CH_3$ | —CH(CH₂)₂ (cyclopropyl) |
| $C_2H_5$ | $C_2H_5$ |
| $C_2H_5$ | $i$-$C_3H_7$ |
| $C_2H_5$ | —CH(CH₂)₂ (cyclopropyl) |
| $(t)C_4H_9$—C₆H₄— | $i$-$C_3H_7$ |

Some practical embodiments for production of the maleamide compound (III) are as follows:

EXAMPLE 26

Maleamide amine salt (X)

To a solution of 2,3-dimethyl-2-aminobutanamide (20.0 g) and triethylamine (300 g) in diethyl ether (400 ml), 2,3-dimethylmaleic anhydride (20.0 g) was portionwise added in 1 hour, and the resultant mixture was allowed to stand at room temperature overnight. The precipitated crystals were collected by filtration to give 46.9 g of triethylamine salt of N-(alpha-isopropyl-alpha-methyl-alpha-carbamoylmethyl)-2,3-dimethylmaleamidic acid. m.p., 115° C.–117° C. Yield, 84.5%.

EXAMPLE 27

Triethylamine salt of N-(alpha-isopropyl-alpha-methyl-alpha-carbamoylmethyl)-2,3-dimethylmaleamidic acid (46.9 g) was dissolved in N,N-dimethylformamide (250 ml), ethyl iodide (25.0 g) was added thereto, and the resultant mixture was stirred at 50° C. for 24 hours. The reaction mixture was poured into water and extracted with chloroform. After concentration of the extract, the residue was added to toluene (100 ml), and the precipitated crystals were collected by filtration to give 23.5 g of N-(2,3-dimethyl-butanamido-2-yl)-2,3-dimethylmaleamidic acid ethyl ester. m.p., 99° C.–101° C. Yield, 63%.

In the same manner as above, the maleamide compounds (III) as shown in Table 15 were obtained.

TABLE 15

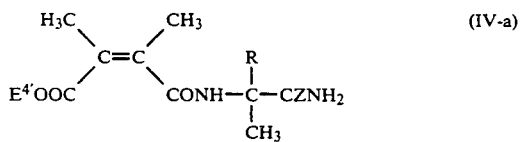

| $E^3$ | R | Physical property |
|---|---|---|
| $CH_3$ | $i\text{-}C_3H_7$ | m.p., 77–80° C. |
| $C_2H_5$ | $i\text{-}C_3H_7$ | m.p., 99–101° C. |
| (t)C$_4$H$_9$—⟨phenyl⟩ | $i\text{-}C_3H_7$ | m.p., 183–185° C. |

The starting material in Procedure (C), i.e. maleamide compound (IV) wherein $E^4$ is a tertiary ammonium cation, corresponds to the maleamide amine salt (X).

The maleamide compound (IV) wherein $E^4$ is an alkali metal cation has the following formula:

wherein R and Z are each as defined above and $E^{4'}$ is an alkali metal cation and can be prepared by reacting the maleamide amine salt (X) with a compound of the formula:

$$E^{4'}\text{-}A \qquad (XII)$$

wherein $E^{4'}$ is as defined above and A is a hydrogen atom, a hydroxyl group, a methoxy group or an ethoxy group in a solvent. This reaction is usually accomplished at a temperature of about 0° C. to 50° C. for a period of about 10 minutes to 3 hours. The compound (XII) may be used in an amount of 1 to 1.2 equivalents to 1 equivalent of the maleamide amine salt (X). In case of A being methoxy or ethoxy, the use of methanol or ethanol as the solvent is preferred. In case of A being hydrogen, the use of N,N-dimethylformamide, methanol or ethanol is favorable. In case of A being hydroxyl, water, methanol or ethanol is preferably employed. The reaction mixture containing the maleamide compound (IV-a) may be as such used in Procedure (C) without isolation of such product.

In the practical use of the butenoic acid derivatives (I), they may be applied in conventional preparation forms such as emulsifiable concentrates, wettable powders, suspensions, granules and solutions in combination with conventional solid or liquid carriers or diluents as well as surface active agents or auxiliary agents. The content of the butenoic acid derivatives (I) as the active ingredient in such preparation forms is usually within a range of about 1 to 90% by weight, preferably of about 1 to 80% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate, synthetic hydrous silicate, etc. As the liquid carrier or diluent, there may be exemplified aromatic hydrocarbons (e.g. xylene, methylnaphthalene), alcohols (e.g. methanol, isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be any of the anionic and non-ionic type of agents. Examples of the surface active agent include anionic surfactants and nonionic surfactants such as alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters and polyoxyethylene sorbitan fatty acid esters. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the present invention are illustratively shown in the following examples wherein parts are by weight.

FORMULATION EXAMPLE 1

Fifty parts of any of Compound Nos. 2, 5, 17, 18, 20, 22+23 (mixture), 34, 42, 52, 81 (trans-form) and 82 (cis-form), 3 parts of calcium ligninsulfonate, 2 parts of sodium laurylsulfate and 45 parts of synthetic hydrous silicate are mixed well while being powdered to obtain a wettable powder.

FORMULATION EXAMPLE 2

Ten parts of any of Compound Nos. 2, 12, 17, 18, 20, 22+23 (mixture), 32, 49, 55, 81 (trans-form) and 82 (trans-form), 14 parts of polyoxyethylenestyrylphenyl ether, 6 parts of calcium dodecylbenzenesulfonate, 70 parts of methanol are mixed well to obtain an emulsifiable concentrate.

FORMULATION EXAMPLE 3

Two parts of any of Compound Nos. 2, 4, 17, 18, 20, 22+23 (mixture), 34, 49, 72, 81 (trans-form) and 82 (trans-form), 1 part of synthetic hydrous silicate, 2 parts of calcium ligninsulfonate, 30 parts of bentonite and 65 parts of kaolin clay are mixed well while being powdered. The mixture is then kneaded with water, granulated and dried to obtain granules.

FORMULATION EXAMPLE 4

Twenty-five parts of any of Compound Nos. 2, 4, 17, 18, 20, 22 +23 (mixture), 49, 72, 81 (trans-form) and 82 (trans-form), 3 parts of polyoxyethylenesorbitan monooleate, 3 parts of CMC and 69 parts of water are mixed well and pulverized until the particle size becomes less than 5 microns to obtain a suspension.

FORMULATION EXAMPLE 5

One part of any of Compound Nos. 41 and 42, 1 part of polyoxyethylenestyrylphenyl ether and 98 parts of water are mixed well to obtain a solution.

FORMULATION EXAMPLE 6

Eighty parts of any of Compound Nos. 2, 5, 17, 18, 20, 22 +23 (mixture), 34, 42, 52, 81 (trans-form) and 82 (cis-form), 3 parts of calcium ligninsulfonate, 2 parts of sodium laurylsulfate and 15 parts of synthetic hydrous silicate are mixed well while being powdered to obtain a wettable powder.

The butenoic acid derivatives (I) thus formulated in any suitable formulation form are useful for the pre-emergence or post-emergence control of undesired weeds by soil or foliar treatment. These treatments include the application to the soil surface prior to or after the transplanting or the incorporation into the soil. The foliar treatment may be effected by spraying the herbicidal composition containing the butenoic acid derivatives (I) over the top of the plants. It may also be applied directly to the weeds if care is taken to keep the chemical off the crop foliage.

The butenoic acid derivatives (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc. Furthermore, they can be used as herbicides applicable not only to agricultural plowed field but also to orchards, pasture lands, lawns, forests, non-agricultural fields, etc.

The dosage rate of the butenoic acid derivatives (I) may vary on prevailing weather conditions, formulation used, prevailing season, mode of application, soil involved, crop and weed species, etc. Generally, however, the dosage rate for application in upland field is from about 0.1 to 50 grams, preferably from about 0.1 to 40 grams, of the active ingredient per are. The dosage rate for application in the non-agricultural fields is from about 1 to 200 grams, preferably from about 2 to 100 grams, of the active ingredient per are. The herbicidal composition of the invention formulated in the form of an emulsifiable concentrate, a wettable powder or a suspension may ordinarily be employed by diluting it with water at a volume of about 1 to 10 liters per are, if necessary, with the addition of an auxiliary agent such as a spreading agent. Examples of the spreading agent include, in addition to the surface active agents as noted above, polyoxyethylene resin acid and its esters, ligninsulfonates, abiettates, dinaphthylmethanedisulfonates, paraffin, etc. The composition formulated in the form of granules may be normally applied as such without dilution.

The biological data of the butenoic acid derivatives (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants. The following compounds were used for comparison.

| Compound No. | Structure | Remarks |
|---|---|---|
| A | quinoline with COOH, N, C(CH3)(C3H7(i)), N-H, =O ring | commercially available herbicide; "immazaquin" |
| B | H2N-triazole-NH structure | commercially available herbicide; "amitrole" |
| C | benzene with COOH, N, C(CH3)(C3H7(i)), N-H, =O | U.S. Pat. No. 4,188,487 |

TEST EXAMPLE 1

Cylindrical plastic pots (diameter, 10 cm; height, 10 cm) were filled with upland field soil, and the seeds of Japanese millet, oats, tall morningglory and velvetleaf were sowed therein and covered with soil. A designated amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined.

TABLE 16

| Compound No. | Dosage (g/are) | Herbicidal activity | | | |
|---|---|---|---|---|---|
| | | Japanese millet | Oats | Tall morning-glory | Velvet-leaf |
| 2 | 20 | 5 | 5 | 5 | 5 |
|   | 5  | 5 | 4 | 5 | 4 |
| 4 | 20 | 5 | 5 | 5 | 5 |
|   | 5  | 5 | 4 | 4 | 4 |
| 5 | 20 | 5 | 4 | 5 | 4 |
| 6 | 20 | 5 | 5 | 5 | 5 |
|   | 5  | 4 | 4 | 4 | 4 |
| 7 | 20 | 4 | 4 | 4 | 4 |
| 8 | 20 | 5 | 4 | 5 | 4 |
| 9 | 20 | 5 | 4 | 5 | 4 |
| 12 | 20 | 5 | 4 | 5 | 4 |
|    | 5  | 5 | 4 | 5 | 4 |
| 13 | 20 | 5 | 5 | 5 | 4 |
|    | 5  | 4 | 4 | 5 | 4 |
| 14 | 20 | 5 | 5 | 5 | 4 |
| 17 | 20 | 5 | 5 | 5 | 5 |
|    | 5  | 5 | 4 | 5 | 5 |
| 18 | 20 | 4 | — | 5 | 4 |
|    | 5  | 3 | — | 4 | 4 |
| 19 | 20 | 5 | — | 5 | 4 |

TABLE 16-continued

| Compound No. | Dosage (g/are) | Japanese millet | Oats | Tall morning-glory | Velvet-leaf |
|---|---|---|---|---|---|
| 20 | 20 | 5 | 5 | 5 | 4 |
|  | 5 | 4 | 4 | 4 | 3 |
| 22 | 20 | 5 | 5 | 5 | 4 |
| 22+23 | 20 | 5 | 5 | 5 | 5 |
|  | 5 | 5 | 5 | 5 | 5 |
| 25 | 5 | 4 | 4 | 5 | 4 |
| 26 | 5 | 4 | 5 | 5 | 4 |
| 27 | 5 | 4 | 4 | 4 | 4 |
| 28 | 5 | 4 | 4 | 5 | 4 |
| 29 | 5 | 4 | 4 | 4 | 4 |
| 30 | 5 | 4 | 4 | 4 | 4 |
| 31 | 5 | 4 | 4 | 5 | 4 |
| 32 | 20 | 4 | 4 | 4 | — |
| 34 | 5 | 4 | 4 | 4 | 4 |
| 35 | 5 | 4 | 4 | 5 | 5 |
| 36 | 5 | 4 | 4 | 4 | 4 |
| 37 | 5 | 4 | 4 | 5 | 4 |
| 38 | 5 | 4 | 4 | 5 | 4 |
| 39 | 5 | 4 | 4 | 4 | 4 |
| 40 | 5 | 4 | 4 | 4 | 4 |
| 41 | 20 | 5 | 5 | 5 | 5 |
|  | 5 | 5 | 4 | 5 | 5 |
| 42 | 20 | 4 | 4 | 4 | 4 |
| 43 | 20 | 4 | 4 | 4 | 4 |
| 44 | 20 | 4 | 4 | 5 | 4 |
| 45 | 20 | 4 | 4 | 5 | 4 |
| 46 | 20 | 4 | 4 | 5 | 4 |
| 47 | 20 | 4 | 4 | 4 | 4 |
| 49 | 20 | 4 | 4 | 5 | 4 |
| 50 | 20 | 4 | 4 | 4 | — |
| 52 | 20 | 5 | 5 | 5 | 4 |
| 53 | 20 | 5 | 4 | 5 | — |
| 54 | 20 | 5 | 4 | 5 | — |
| 55 | 20 | 5 | 5 | 5 | 5 |
| 56 | 20 | 4 | 4 | 4 | — |
| 57 | 20 | 4 | 4 | 4 | — |
| 58 | 20 | 4 | 4 | 4 | — |
| 59 | 20 | 5 | 4 | 4 | — |
| 61 | 20 | 4 | 4 | 4 | — |
| 62 | 20 | 5 | 4 | 5 | 4 |
| 63 | 20 | 4 | 4 | 4 | — |
| 64 | 20 | 4 | 4 | 4 | — |
| 65 | 20 | 5 | 4 | 4 | — |
| 69 | 20 | 4 | 4 | 4 | — |
| 70 | 20 | 4 | 4 | 4 | 4 |
| 72 | 20 | 5 | 5 | 5 | 5 |
| 73 | 20 | 5 | 5 | 4 | 4 |
| 74 | 20 | 4 | 4 | 4 | 4 |
| 76 | 20 | 5 | 5 | 5 | 4 |
| 77 | 20 | 5 | 5 | 5 | 4 |
| 78 | 20 | 5 | 5 | 5 | 5 |
| 79 | 20 | 5 | 5 | 5 | 5 |
| 80 | 20 | 5 | 5 | 5 | 5 |
| 81 | 20 | 5 | 5 | 5 | 5 |
| (trans) | 5 | 5 | 5 | 5 | 5 |
| 82 | 20 | 4 | 4 | 4 | 4 |
| (trans) |  |  |  |  |  |
| 82 | 20 | 4 | 4 | 4 | — |
| (cis) |  |  |  |  |  |
| B | 20 | 2 | 2 | 3 | 2 |
|  | 5 | 1 | 1 | 2 | 1 |
| C | 20 | 3 | 4 | 5 | 5 |
|  | 5 | 2 | 3 | 4 | 4 |

TEST EXAMPLE 2

Cylindrical plastic pots (diameter, 10 cm; height, 10 cm) were filled with upland field soil, and the seeds of Japanese millet, oats, radish and velvetleaf were sowed therein and cultivated in a greenhouse for 10 days. A designated amount of the test compound formulated in an emulsifiable concentrate according to Formulation Example 2 was diluted with water containing a spreading agent, and the dilution with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined.

The results are shown in Table 17.

TABLE 17

| Compound No. | Dosage (g/are) | Japanese millet | Oats | Radish | Velvet-leaf |
|---|---|---|---|---|---|
| 2 | 20 | 5 | 5 | 5 | 5 |
|  | 5 | 5 | 5 | 5 | 4 |
| 4 | 20 | 5 | 5 | 5 | 5 |
|  | 5 | 5 | 5 | 5 | 4 |
| 5 | 20 | 5 | 5 | 5 | 5 |
| 6 | 20 | 5 | 5 | 5 | 5 |
|  | 5 | 5 | 5 | 5 | 5 |
| 7 | 20 | 5 | 5 | 5 | — |
| 8 | 20 | 5 | 5 | 5 | 5 |
|  | 5 | 5 | 5 | 5 | 5 |
| 9 | 20 | 5 | 5 | 5 | 5 |
|  | 5 | 4 | 4 | 5 | 5 |
| 12 | 20 | 5 | 5 | 5 | 5 |
|  | 5 | 5 | 5 | 5 | 4 |
| 13 | 20 | 5 | 5 | 5 | 4 |
|  | 5 | 5 | 5 | 5 | 3 |
| 14 | 20 | 5 | 5 | 5 | 4 |
|  | 5 | 5 | 5 | 5 | 4 |
| 15 | 20 | 4 | 5 | 5 | 4 |
| 17 | 20 | 5 | 5 | 5 | 5 |
|  | 5 | 5 | 5 | 5 | 4 |
| 18 | 20 | 5 | 5 | 5 | — |
|  | 5 | 5 | 3 | 5 | — |
| 19 | 20 | 5 | 5 | 5 | — |
|  | 5 | 5 | 3 | 5 | — |
| 20 | 20 | 5 | 5 | 5 | 5 |
|  | 5 | 4 | 4 | 5 | 4 |
| 22 | 5 | 5 | 5 | 5 | 4 |
| 22+23 | 20 | 5 | 5 | 5 | 4 |
|  | 5 | 4 | 5 | 5 | 3 |
| 25 | 5 | 4 | 4 | 5 | 4 |
| 26 | 5 | 5 | 5 | 5 | 4 |
| 27 | 5 | 4 | 5 | 5 | 4 |
| 28 | 5 | 5 | 5 | 5 | 4 |
| 29 | 5 | 5 | 4 | 5 | 4 |
| 30 | 5 | 5 | 5 | 5 | 5 |
| 31 | 5 | 5 | 5 | 5 | 4 |
| 32 | 5 | 4 | 4 | 5 | — |
| 33 | 5 | — | — | 4 | — |
| 34 | 5 | 5 | 5 | 5 | 4 |
| 35 | 5 | 4 | 5 | 5 | 4 |
| 36 | 5 | 5 | 5 | 5 | 4 |
| 37 | 5 | 5 | 5 | 5 | 4 |
| 38 | 5 | 5 | 5 | 5 | 4 |
| 39 | 5 | 4 | 5 | 5 | 5 |
| 40 | 5 | 5 | 5 | 5 | 5 |
| 41 | 5 | 5 | 5 | 5 | 5 |
| 42 | 5 | 4 | 4 | 5 | 4 |
| 43 | 5 | 5 | 5 | 5 | 4 |
| 44 | 5 | 5 | 5 | 5 | 4 |
| 45 | 5 | 5 | 5 | 5 | 4 |
| 46 | 5 | 5 | 5 | 5 | 4 |
| 47 | 5 | 5 | 5 | 5 | 4 |
| 48 | 5 | 4 | 4 | 5 | — |
| 49 | 5 | 5 | 5 | 5 | 4 |
| 52 | 5 | 5 | 4 | 5 | 4 |
| 54 | 5 | 5 | 5 | 5 | 4 |
| 55 | 5 | 5 | 5 | 5 | 4 |
| 59 | 5 | 5 | 5 | 5 | 4 |
| 72 | 5 | 5 | 5 | 5 | 5 |
| 78 | 5 | 4 | 4 | 5 | 4 |
| 79 | 5 | 5 | 5 | 5 | 4 |
| 80 | 5 | 5 | 5 | 5 | 5 |
| 81 | 20 | 5 | 5 | 5 | 5 |
| (trans) | 5 | 5 | 5 | 5 | 5 |
| 82 | 5 | 5 | 5 | 5 | 4 |
| (trans) |  |  |  |  |  |
| 82 | 5 | — | 4 | 5 | — |
| (cis) |  |  |  |  |  |
| B | 20 | 4 | 3 | 4 | 4 |

TABLE 17-continued

| Compound No. | Dosage (g/are) | Herbicidal activity | | | |
|---|---|---|---|---|---|
| | | Japanese millet | Oats | Radish | Velvet-leaf |
| | 5 | 3 | 1 | 3 | 3 |

TEST EXAMPLE 3

Vats (33 cm×23 cm×11 cm) were filled with upland field soil, and the seeds of soybean, cotton, corn, wheat, tall morningglory, common cocklevur, velvetleaf, sicklepod, black nightshade, cleavers, barnyardgrass, common chickweek, parsion speedwell, johnsongrass, green foxtail and wild oats were sowed therein in 1 to 2 cm depth. A designated amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined.

The results are shown in Table 18.

TABLE 18

| Compound No. | Dosage (g/a) | Soybean | Cotton | Corn | Wheat | Tall morning-glory | Common cocklebur | Velvet-leaf | Sicklepod | Black nightshade | Cleavers | Barn-yardgrass | Common chickweed | Persian speedwell | Johnsongrass | Green foxtail | Wild oat |
|---|---|---|---|---|---|---|---|---|---|---|---|---|---|---|---|---|---|
| 2 | 7 | — | 2 | — | — | 5 | — | 4 | 5 | — | — | 5 | — | — | 5 | 5 | — |
|   | 1.25 | — | 1 | 0 | — | 3 | 3 | 4 | 4 | — | — | 5 | — | — | 5 | 5 | — |
|   | 0.32 | — | 0 | 0 | — | 2 | 0 | 2 | 4 | — | — | 3 | — | — | 3 | 4 | — |
| 4 | 1.25 | 2 | 0 | 2 | — | — | — | — | — | 4 | 4 | 4 | 5 | 4 | 4 | 4 | 4 |
| 5 | 2.5 | 1 | 1 | 0 | — | — | — | — | — | 4 | 4 | 4 | 4 | 4 | 4 | 5 | 4 |
| 6 | 1.25 | 2 | 2 | 2 | — | — | — | — | — | 4 | 4 | 5 | 4 | 5 | 5 | 5 | 4 |
| 12 | 2.5 | 2 | 1 | 2 | — | — | — | — | — | 4 | — | 4 | 4 | — | 4 | 4 | 4 |
| 13 | 2.5 | 2 | 1 | 2 | — | — | — | — | — | 4 | — | 4 | 4 | — | 4 | 4 | 4 |
| 17 | 5 | 1 | 2 | 1 | — | 4 | 4 | 4 | 4 | 4 | — | 5 | — | — | 5 | 5 | — |
|   | 1.25 | 0 | 0 | — | — | 2 | 1 | 2 | 4 | 3 | — | 2 | — | — | 3 | 4 | — |
|   | 0.32 | — | 0 | 0 | — | — | 0 | 0 | 4 | 5 | — | — | — | — | — | — | — |
| 18 | 10 | — | 0 | — | — | 4 | — | 4 | 4 | 4 | — | 5 | 5 | 5 | 5 | 5 | — |
| 20 | 5 | — | 2 | — | — | 4 | 4 | 4 | 4 | 4 | — | 4 | — | — | 4 | 4 | — |
| 22+23 | 5 | 1 | 0 | — | — | 3 | 2 | 2 | 4 | 4 | — | 3 | — | — | 4 | 4 | — |
|   | 1.25 | 0 | 0 | — | — | 2 | — | 1 | 4 | 4 | — | — | — | — | — | — | — |
|   | 0.32 | 2 | 2 | — | — | 4 | — | — | 4 | 4 | — | 4 | — | — | 4 | 4 | — |
| 25 | 2.5 | 3 | 1 | 0 | — | — | — | — | — | — | — | 4 | — | — | 4 | 4 | — |
| 26 | 2.5 | 3 | 2 | 3 | — | 4 | — | — | 4 | — | — | 4 | — | — | 4 | 4 | — |
| 30 | 2.5 | 3 | 1 | 2 | — | 4 | — | — | 4 | — | — | 4 | — | — | 4 | 4 | — |
| 31 | 2.5 | 3 | 1 | 2 | — | 4 | — | — | 4 | — | — | 4 | — | — | 4 | 4 | — |
| 34 | 2.5 | 3 | 0 | 1 | — | 4 | — | — | 4 | 4 | — | 4 | — | — | 4 | 4 | — |
| 35 | 2.5 | 3 | 2 | 1 | — | 4 | — | — | 4 | — | — | 4 | — | — | 4 | 4 | — |
| 36 | 2.5 | 0 | 0 | — | — | — | — | — | — | — | — | 4 | — | — | 4 | 4 | — |
| 37 | 2.5 | — | 1 | — | — | 4 | — | 4 | 4 | 4 | — | 4 | — | — | 4 | 4 | — |
| 38 | 2.5 | — | 0 | — | — | 4 | — | 4 | 4 | — | — | 4 | — | — | 4 | 4 | — |
| 39 | 5 | 1 | 2 | 1 | — | 4 | — | 4 | — | — | — | 4 | — | — | 4 | 4 | — |
| 40 | 2.5 | — | 0 | 0 | — | 4 | — | — | 4 | — | — | 4 | — | — | 4 | 4 | — |
| 43 | 2.5 | 0 | 1 | 1 | — | 4 | 5 | 4 | — | — | — | 4 | — | — | 5 | 5 | — |
| 46 | 10 | — | — | — | — | 5 | — | 4 | 5 | — | — | 5 | — | — | 4 | 4 | — |
| 49 | 2.5 | — | 2 | 0 | — | 5 | 5 | 5 | 5 | 4 | — | 5 | — | — | 4 | 4 | — |
| 52 | 10 | — | 1 | 2 | — | 4 | 4 | 4 | — | 5 | — | 5 | — | — | 5 | 5 | — |
| 53 | 5 | 3 | — | 1 | — | 5 | 4 | 4 | 4 | 5 | — | 5 | — | — | 5 | 5 | — |
|   | 10 | 3 | 2 | 1 | — | 4 | 4 | 4 | 4 | 4 | — | 5 | — | — | 5 | 5 | — |
| 55 | 5 | — | 0 | 0 | — | 4 | 4 | — | — | 4 | — | 4 | — | — | 4 | 4 | — |
|   | 10 | — | 0 | 0 | — | 4 | 4 | 4 | — | 4 | — | 4 | — | — | 4 | 4 | — |
| 65 | 10 | 0 | 2 | 0 | — | 4 | — | — | 4 | — | — | 4 | — | — | 4 | 4 | — |
|   | 5 | 0 | 2 | 0 | — | 4 | — | — | 4 | — | — | 4 | — | — | 4 | 4 | — |
| 72 | 10 | — | 0 | 0 | — | 4 | 4 | 4 | 4 | 4 | — | 4 | — | — | 4 | 4 | — |
|   | 5 | 0 | 2 | 0 | — | 4 | 3 | 3 | 3 | 3 | — | 4 | — | — | 4 | 4 | — |
| 76 | 10 | — | 0 | 0 | — | 4 | — | 3 | — | 3 | — | 4 | — | — | 4 | 4 | — |
|   | 5 | — | 2 | 0 | — | 4 | 3 | 3 | 3 | — | — | 4 | — | — | 4 | 4 | — |
| 77 | 10 | 1 | — | 2 | — | 5 | — | 3 | — | 3 | — | 4 | — | — | 4 | 4 | — |
|   | 5 | — | 1 | 0 | — | 5 | 4 | 3 | 4 | — | — | 4 | — | — | 4 | 4 | — |
| 78 | 10 | — | — | 0 | — | 4 | — | 4 | — | 4 | — | 4 | — | — | 4 | 4 | — |
|   | 5 | — | 1 | — | — | 4 | 3 | 3 | 3 | 4 | — | 4 | — | — | 4 | 3 | — |
| 80 | 10 | — | — | 2 | — | 3 | — | — | — | 4 | — | 4 | — | — | 3 | 5 | — |
| 81 (trans) | 0.63 | 1 | 1 | 0 | — | — | — | — | — | — | — | 5 | — | — | 5 | 5 | — |
|   | 0.16 | 0 | 0 | 0 | — | — | — | — | — | 3 | — | 4 | — | — | 4 | 5 | — |

TABLE 18-continued

| Compound No. | Dosage (g/a) | Soybean | Cotton | Corn | Wheat | Tall morning-glory | Common cocklebur | Velvet-leaf | Sicklepod | Black nightshade | Cleavers | Barn-yardgrass | Common chickweed | Persian speedwell | Johnsongrass | Green foxtail | Wild oat |
|---|---|---|---|---|---|---|---|---|---|---|---|---|---|---|---|---|---|
| 82 (trans) | 5 | 1 | 1 | 1 | 1 | — | — | — | — | 4 | 4 | 4 | — | 4 | — | — | 4 |
| A | 5 | 0 | 4 | 5 | 4 | 3 | 1 | 2 | 0 | 3 | 3 | 3 | — | 3 | 3 | 3 | 3 |
| B | 5 | 0 | 0 | 0 | — | 0 | 0 | 1 | 0 | 2 | — | 1 | — | — | 0 | 3 | — |

TEST EXAMPLE 4

Vats (33 cm × 23 cm × 11 cm) were filled with upland field soil, and the seeds of wheat, cotton, corn, soybean, tall morningglory, common cocklebur, velvetleaf, sicklepod, black nightshade, common chickweed, persion speedwell, cleavers, barnyardgrass, johnsongrass, green foxtail and wild oats were sowed therein and cultivated in a greenhouse for 18 days. A designated amount of the test compound formulated in an emulsifiable concentrate according to Formulation Example 2 was diluted with water, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although they varied depending on their species.

The results are shown in Table 19.

TABLE 19

| Compound No. | Dosage (g/a) | Wheat | Cotton | Corn | Soybean | Tall morning-glory | Common cocklebur | Velvet-leaf | Sicklepod | Black nightshade | Common chickweed | Persian speedwell | Cleavers | Barn-yardgrass | Johnsongrass | Green foxtail | Wild oat |
|---|---|---|---|---|---|---|---|---|---|---|---|---|---|---|---|---|---|
| 2 | 10 | 1 | — | — | — | 5 | 5 | 4 | 5 | 5 | 4 | — | — | 5 | 5 | 5 | — |
| 4 | 2.5 | 0 | — | — | — | 5 | 4 | 3 | 5 | 5 | 4 | 5 | 5 | 5 | 5 | 5 | 4 |
| 5 | 2.5 | — | 1 | — | — | 4 | 4 | 4 | — | 4 | 4 | 5 | 4 | 4 | 4 | 4 | 4 |
| 9 | 2.5 | — | — | 1 | — | 4 | 4 | — | — | 4 | 5 | 5 | 4 | 4 | 4 | 4 | 4 |
| 12 | 2.5 | — | 1 | — | — | 4 | 4 | 4 | — | 4 | — | 5 | 4 | 4 | 4 | 4 | 4 |
| 13 | 2.5 | — | 2 | — | — | 4 | 4 | — | — | 4 | 4 | 5 | 4 | 4 | 4 | 4 | 4 |
| 17 | 10 | — | — | — | — | 5 | 4 | 2 | 5 | 5 | 5 | 5 | 5 | 5 | 5 | 5 | — |
| 18 | 2.5 | — | — | 0 | — | 4 | 3 | — | 4 | 5 | — | — | — | 5 | 5 | 5 | — |
| 19 | 2.5 | — | — | 0 | — | 4 | 4 | 4 | 4 | 5 | — | — | — | 4 | — | — | — |
| 20 | 2.5 | — | — | — | — | 5 | 4 | 3 | 2 | 4 | 5 | — | 5 | 5 | 5 | 5 | 5 |
| 22+23 | 2.5 | — | 3 | — | — | 4 | 4 | — | 5 | 4 | 5 | 4 | 4 | 4 | 4 | 4 | 4 |
| 25 | 2.5 | — | 2 | — | — | 4 | 4 | — | 5 | 4 | 5 | 5 | 4 | 4 | 4 | 4 | 4 |
| 26 | 2.5 | — | 2 | — | — | 4 | 4 | — | 5 | 4 | 4 | 5 | 4 | 4 | 4 | 4 | 4 |
| 29 | 2.5 | — | 2 | — | — | 4 | 4 | — | 5 | 5 | 4 | 5 | 4 | 4 | 4 | 4 | 4 |
| 30 | 2.5 | — | 3 | — | — | 4 | 4 | — | 5 | 4 | 4 | 5 | 4 | 4 | 4 | 4 | 4 |
| 31 | 2.5 | — | 3 | — | — | 4 | 4 | — | 5 | 5 | 5 | 5 | 5 | 4 | 4 | 4 | 4 |
| 35 | 2.5 | — | 2 | — | — | 5 | 4 | — | 5 | 4 | 4 | 4 | 4 | 4 | 4 | 4 | 4 |
| 36 | 2.5 | — | — | — | — | 4 | 4 | — | 5 | 4 | 4 | 5 | 5 | 4 | 4 | 4 | 4 |
| 38 | 2.5 | — | 1 | — | — | 4 | 4 | — | 5 | 5 | 4 | 4 | 4 | 4 | 4 | 4 | 4 |
| 39 | 2.5 | — | — | — | — | 4 | — | — | 5 | 5 | — | 5 | 4 | 4 | 4 | 4 | 4 |
| 40 | 2.5 | — | — | — | — | 5 | 4 | — | — | 4 | 4 | 5 | — | 4 | 4 | 4 | 4 |
| 42 | 2.5 | — | — | — | — | 5 | 4 | — | — | 4 | 4 | 4 | — | 4 | 4 | 4 | 4 |
| 45 | 2.5 | — | — | — | — | 5 | — | — | 5 | 5 | — | 5 | — | 4 | 4 | 4 | 4 |
| 49 | 2.5 | — | — | — | 0 | 4 | — | — | — | 5 | — | — | — | — | — | — | 4 |
| 50 | 10 | — | — | — | 0 | 3 | 4 | — | 4 | 4 | — | — | — | 3 | 3 | 3 | — |
| 52 | 5 | — | — | — | — | 5 | 3 | — | 3 | 4 | — | — | — | 4 | 4 | 4 | — |
|    | 2.5 | — | — | 0 | — | 4 | 4 | — | 5 | 4 | — | — | — | 4 | 4 | 4 | — |
| 54 | 10 | — | — | — | 0 | 3 | — | — | 3 | 4 | — | — | — | 3 | 3 | 3 | — |
|    | 5 | — | — | 0 | — | 4 | 4 | — | 5 | 5 | — | — | — | 4 | 4 | 4 | — |
| 55 | 5 | — | — | — | — | 4 | — | — | 4 | 5 | — | — | — | 4 | 4 | — | — |
|    | 2.5 | — | — | 0 | — | — | — | — | — | 4 | — | — | — | — | — | — | — |
| 57 | 10 | — | — | 0 | — | 4 | 4 | — | 5 | 5 | — | — | — | 4 | 4 | 4 | — |
|    | 5 | — | — | 0 | — | 4 | 3 | — | 4 | 5 | — | — | — | 3 | 3 | 3 | — |
| 59 | 10 | — | — | 0 | 2 | 3 | 4 | — | 4 | 5 | — | — | — | 3 | 3 | 3 | — |
| 66 | 10 | — | — | 0 | 0 | 4 | — | — | 4 | 4 | — | — | — | 3 | 3 | — | — |
| 67 | 10 | — | — | 0 | 0 | 4 | — | — | 4 | 5 | — | — | — | 3 | 4 | 3 | 0 |
| 68 | 10 | — | — | 0 | 0 | 4 | — | — | 4 | 5 | — | — | — | — | 5 | — | 0 |
| 70 | 10 | — | — | 0 | 0 | — | 4 | — | — | 5 | — | — | — | 4 | 4 | — | — |
| 71 | 10 | — | — | 0 | 0 | 4 | 4 | — | 3 | 4 | — | — | — | — | 3 | 3 | — |
|    | 2.5 | — | — | 0 | 0 | 4 | — | — | 4 | 4 | — | — | — | 4 | 4 | 4 | — |
| 72 | 10 | — | — | 0 | — | 4 | — | — | 4 | 4 | — | — | — | 4 | 4 | 4 | — |
|    | 5 | — | — | — | — | 4 | — | — | 4 | 4 | — | — | — | 4 | 4 | 4 | — |

TABLE 19-continued

| Compound No. | Dosage (g/a) | Wheat | Cotton | Corn | Soybean | Tall morning-glory | Common cocklebur | Velvet-leaf | Sicklepod | Black nightshade | Common chickweed | Persian speedwell | Cleavers | Barn-yardgrass | Johnsongrass | Green foxtail | Wild oat |
|---|---|---|---|---|---|---|---|---|---|---|---|---|---|---|---|---|---|
| 75 | 2.5 | — | — | 2 | — | 4 | 4 | — | — | 4 | — | — | — | 3 | 3 | 3 | — |
|  | 10 | — | — | 0 | — | 4 | 4 | — | 5 | 5 | — | — | — | 4 | 5 | 4 | — |
|  | 5 | — | — | 0 | 2 | 4 | 4 | — | 4 | 4 | — | — | — | 4 | 5 | 4 | — |
|  | 2.5 | — | — | 0 | 2 | 3 | 3 | — | 4 | 4 | — | — | — | 4 | 4 | 3 | — |
| 76 | 10 | — | — | — | — | 4 | — | — | 5 | 4 | — | — | — | 4 | 4 | 4 | — |
|  | 5 | — | — | 1 | — | 4 | 4 | — | 4 | 4 | — | — | — | 3 | 4 | 4 | — |
| 79 | 2.5 | — | — | — | — | 3 | 3 | — | 3 | 4 | — | — | — | 4 | 4 | 3 | — |
| 80 | 10 | — | — | — | — | 4 | 4 | — | 5 | 5 | — | — | — | 4 | 4 | 4 | — |
|  | 5 | — | — | — | 2 | 4 | 4 | — | 5 | 4 | — | — | — | 4 | 4 | 4 | — |
| 81 (trans) | 2.5 | — | — | — | — | 4 | — | — | 5 | 4 | — | — | — | 4 | 4 | 3 | — |
|  | 0.63 | — | — | — | — | — | — | — | — | — | — | — | — | — | — | — | — |
| 82 (cis) | 10 | — | — | 0 | 0 | — | — | — | — | 4 | — | 4 | — | — | 4 | 4 | — |
| A | 10 | — | 3 | — | — | 3 | 3 | 0 | 0 | 4 | — | — | — | 5 | 4 | 2 | — |
|  | 2.5 | — | 3 | 3 | — | 2 | 3 | 0 | 0 | 3 | — | — | 2 | 3 | 2 | 2 | — |
| B | 10 | — | — | 3 | 4 | 2 | 2 | — | 3 | 3 | 3 | 3 | — | 3 | 3 | 3 | 3 |
|  | 5 | — | 1 | 2 | 4 | 1 | 1 | — | 2 | 2 | — | — | 2 | 2 | 2 | 2 | — |
|  | 2.5 | — | 1 | 2 | 3 | 0 | 1 | 3 | 2 | 2 | 2 | 2 | 2 | 2 | 2 | 2 | 1 |

TEST EXAMPLE 5

Vats (33 cm×23 cm×11 cm) were filled with upland field soil, and the seeds of tall morningglory, common cocklebur, velvetleaf, sicklepod, black nightshade, cleavers, common chickweed, persian speedwell, barnyardgrass, johnsongrass, green foxtail and wild oat were sowed therein in 1 to 2 cm depth. A designated amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined.

The results are shown in Table 20.

TABLE 20

| | | Herbicidal activity | | | | | | | | | | | |
|---|---|---|---|---|---|---|---|---|---|---|---|---|---|
| Compound No. | Dosage (g/are) | Tall morning-glory | Common cock-lebur | Velvet-leaf | Sickle-pod | Black night-shade | Cleavers | Common chick-weed | Persian speed-well | Barn-yard-grass | John-son-grass | Green fox-tail | Wild oat |
| 29 | 5 | 4 | 4 | 4 | 4 | 5 | 4 | 4 | 4 | 5 | 5 | 5 | 4 |
| 43 | 10 | 4 | 4 | 4 | — | 4 | 4 | 4 | 4 | 4 | 4 | 5 | 4 |
| 44 | 10 | 4 | — | 4 | — | 4 | 4 | — | 4 | 4 | 4 | 4 | 4 |
| A | 5 | 3 | 3 | 2 | 2 | 3 | 3 | — | 3 | 3 | 3 | 3 | 3 |
| B | 10 | 2 | 2 | 0 | — | 2 | 2 | — | 1 | 1 | 2 | 3 | 1 |

TEST EXAMPLE 6

Vats (12 cm×17 cm×7 cm) were filled with upland field soil, and the seeds of wheat, cleavers, persian speedwell, common chickweed and wild oat were sowed therein in 1 to 2 cm depth. A designated amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined.

The results are shown in Table 21.

TABLE 21

| | | Herbicidal activity | | | |
|---|---|---|---|---|---|
| Compound No. | Dosage (g/are) | Wheat | Cleavers | Persian speed-well | Common chick-weed | Wild oat |
| 30 | 1.25 | 1 | — | 5 | 4 | — |
| 34 | 2.5 | 1 | 4 | 4 | — | — |
| 35 | 5 | 1 | — | 4 | 4 | 4 |
| 38 | 5 | 1 | — | 4 | 4 | 4 |
| 39 | 1.25 | 1 | 4 | 4 | 4 | 4 |
| 40 | 0.32 | 0 | 4 | 4 | — | 4 |
| A | 5 | 4 | 4 | 3 | — | 3 |

TEST EXAMPLE 7

Vats (12 cm×17 cm×7 cm) were filled with upland field soil, and the seeds of wheat, cleavers, common chickweed, persian speedwell and wild oat were sowed therein and cultivated in a greenhouse for 18 days. A designated amount of the test compound formulated in an emulsifiable concentrate according to Formulation Example 2 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. At the time of the application, the test plants were generally at the 1 to 4 leaf stage and in 2 to 12 cm height, although they varied depending on their species.

The results are shown in Table 22.

TABLE 22

| | | Herbicidal activity | | | |
|---|---|---|---|---|---|
| Compound No. | Dosage (g/are) | Wheat | Cleavers | Common chick-weed | Persian speed-well | Wild oat |
| 25 | 0.32 | 0 | 4 | — | — | 4 |
| 26 | 0.32 | 1 | — | — | 4 | 4 |
| 30 | 0.32 | 1 | — | — | 4 | 4 |
| 31 | 0.32 | 1 | — | 4 | 4 | 4 |
| 34 | 1.25 | 1 | 4 | — | 4 | 4 |
| 35 | 0.32 | 1 | — | 4 | 5 | 4 |
| 40 | 0.32 | 1 | 4 | — | 4 | 4 |
| B | 2.5 | 3 | 2 | 2 | 2 | 2 |

TEST EXAMPLE 8

Vats (33 cm×23 cm×11 cm) were filled with upland field soil, and the seeds of tall morningglory, common cocklebur, velvetleaf, black nightshade, cleavers, common chickweed, persian speedwell, barnyardgrass, johnsongrass, green foxtail and wild oat were sowed therein and cultivated in a greenhouse for 18 days. A designated amount of the test compound formulated in an emulsifiable concentrate according to Formulation Example 2 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although they varied depending on their species.

The results are shown in Table 23.

TABLE 23

| | | Herbicidal activity | | | | | | | | | | |
|---|---|---|---|---|---|---|---|---|---|---|---|---|
| Compound No. | Dosage (g/are) | Tall morning-glory | Common cock-lebur | Velvet-leaf | Black night-shade | Cleavers | Common chick-weed | Persian speed-well | Barn-yard-grass | Johnson-grass | Green fox-tail | Wild oat |
| 43 | 10 | 5 | 4 | 4 | 5 | 4 | 4 | 4 | 4 | 4 | 4 | 4 |
| 44 | 10 | 5 | 4 | 4 | 5 | 4 | 5 | 5 | 4 | 5 | 4 | 4 |
| 46 | 10 | 5 | 4 | 4 | 5 | 4 | 5 | 4 | 4 | 4 | 4 | 4 |
| 49 | 10 | 5 | 4 | 4 | 5 | 4 | 5 | 4 | 4 | 4 | 4 | 4 |

TABLE 23-continued

| | | Herbicidal activity | | | | | | | | | |
|---|---|---|---|---|---|---|---|---|---|---|---|
| Compound No. | Dosage (g/are) | Tall morning-glory | Common cock-lebur | Velvet-leaf | Black night-shade | Cleavers | Common chick-weed | Persian speed-well | Barn-yard-grass | Johnson-grass | Green fox-tail | Wild oat |
| B | 10 | 2 | 2 | — | 3 | 2 | 3 | 3 | 3 | 3 | 3 | 3 |

What is claimed is:

1. A butenoic acid derivative of the formula:

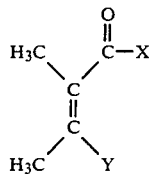

(I)

wherein
X is a hydroxyl group;
a group of the formula: $-OE^1$
wherein $E^1$ is a $C_1-C_8$ alkyl group, a $C_3-C_{12}$ alkenyl group, a $C_3-C_{10}$ alkynyl group, a $C_1-C_{12}$ alkoxy($C_1-C_{12}$)alkyl group, a halo($C_1-C_{12}$)alkyl group, a phenyl($C_1-C_{12}$)alkyl group optionally substituted with one or more $C_1-C_{12}$ alkyl groups on the benzene ring or a phenoxy($C_1-C_{12}$)alkyl group optionally substituted with one or more $C_1-C_{12}$ alkyl groups on the benzene ring or a salt-forming cation selected from the group consisting of ammonium, organic ammonium, alkali metals, alkaline earth metals, manganese (II), copper (II), iron (II), iron (III), zinc (II), cobalt (II), lead (II), silver (I), aluminium (III) and nickel (II);
a group of the formula:

wherein $E^2$ is a hydrogen atom, a hydroxyl group, a $C_1-C_{12}$ alkyl group, a $C_3-C_6$ cycloalkyl group, a $C_1-C_3$ alkoxy($C_1-C_{12}$)alkyl group, a hydroxy-($C_1-C_{12}$) alkyl group, a cyano($C_1-C_{12}$) alkyl group, a $C_3-C_{12}$ alkenyl group, a $C_3-C_{12}$ alkynyl group, a carbamoyl(-$C_1-C_{12}$) alkyl group, phenyl($C_1-C_4$) alkyl group, a $C_1-C_3$ alkoxycarbonyl($C_1-C_{12}$)alkyl group or a tetrahydrofurfuryl group;
or either one of the following groups:

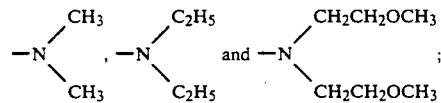

Y is either one of the following formulas:

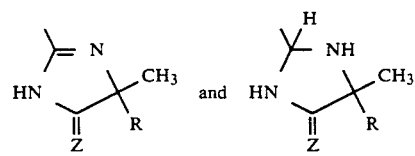

wherein Z is an oxygen atom or a sulfur atom and R is an ethyl group, an isopropyl group or a cyclopropyl group, or their salt forms;
or X and Y may be combined together to represent either one of the following formulas:

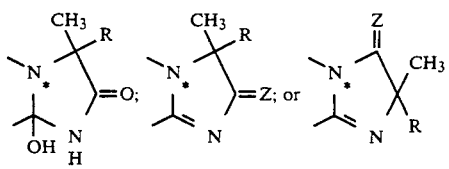

wherein Z and R are each as defined above and a nitrogen atom bearing an asterisk (*) is bonded to the carbonyl carbon atom;
with the provisos that
i) when $E^1$ is a $C_1-C_8$ alkyl group, a $C_3-C_{12}$ alkenyl group, a $C_3-C_{10}$ alkynyl group, a $C_1-C_{12}$ alkoxy($C_1-C_{12}$)alkyl group, a halo($C_1-C_{12}$)alkyl group, a phenyl($C_1-C_{12}$)alkyl group optionally substituted with one or more $C_1-C_{12}$ alkyl groups on the benzene ring or a phenoxy($C_1-C_{12}$)alkyl group optionally substituted with one or more $C_1-C_{12}$ alkyl groups on the benzene ring, Y represents a group of the formula:

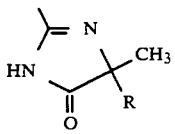

wherein R is as defined above;
ii) when $E^1$ is the salt-forming cation selected from the group consisting of ammonium, organic ammonium, alkali metals, alkaline earth metals, manganese (II), copper (II), iron (II), iron (III), zinc (II), cobalt (II), lead (II), silver (I), aluminium (III) and nickel (II), Y represents a compound of the formula:

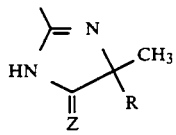

wherein R and Z are each as defined above; and
iii) when X is either one of the following formulas:

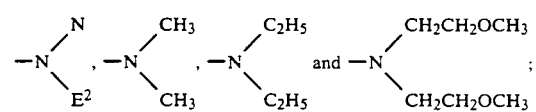

wherein $E^2$ is as defined above, Y represents a compound of the formula:

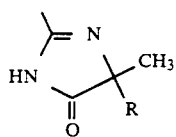

wherein R is as defined above.

2. 5-Hydroxy-2-isopropyl-2,6,7-trimethyl-H-1,4-diazabicyclo[3.3.0]oct-6-ene-3,8-dione.
3. 2-Methyl-3-(5'-isopropyl-5'-methyl-4'-oxo-2'-imidazolin-2'-yl)-(Z)-2-butenoic acid.
4. 2-Isopropyl-2,6,7-trimethyl-1,4-diazabicyclo[3.3.0]oct-4,6-diene-3,8-dione.
5. 2-Methyl-3-(trans-5'-isopropyl-5'-methyl-4'-thioxoimidazolidin-2'-yl)-(Z)-2-butenoic acid.
6. Aluminium 2-methyl-3-(5,-isopropyl-5'-methyl-4'-oxo-2'-imidazolin-2'-yl)-(Z)-2-butenoate.
7. 2-Methyl-3-(trans-5'-isopropyl-5'-methyl-4'-oxoimidazolidin-2'-yl)-(Z)-2-butenoic acid.
8. 2-Methyl-3-(5'-isopropyl-5'-methyl-4'-oxo-2'-imidazolin-2'-yl)-(Z)-2-butenoic acid amide.
9. A butenoic acid derivative of the formula:

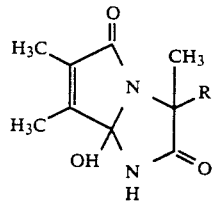   (I-a)

wherein R is an ethyl group, an isopropyl group or a cyclopropyl group.

10. A butenoic acid derivative of the formula:

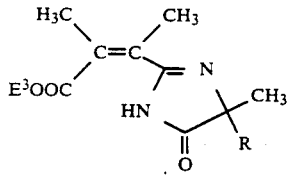   (I-b)

wherein R is an ethyl group, an isopropyl group or a cyclopropyl group and $E^3$ is a $C_1$-$C_8$ alkyl group, a $C_3$-$C_{12}$ alkenyl group, a $C_3$-$C_{10}$ alkynyl group, a $C_1$-$C_{12}$ alkoxy-($C_1$-$C_{12}$)alkyl group, a halo($C_1$-$C_{12}$)alkyl group or a phenyl-($C_1$-$C_{12}$)alkyl group optionally substituted with one or more $C_1$-$C_{12}$ alkyl groups or a phenoxy($C_1$-$C_{12}$)alkyl group optionally substituted with one or more $C_1$-$C_{12}$ alkyl groups.

11. A butenoic acid derivative of the formula:

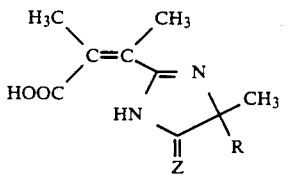   (I-c)

wherein R is an ethyl group, an isopropyl group or a cyclopropyl group and Z is an oxygen atom or a sulfur atom, or its salt.

12. A butenoic acid derivative of the formula:

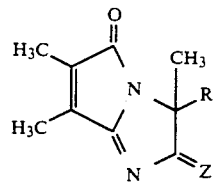   (I-d)

wherein R is an ethyl group, an isopropyl group or a cyclopropyl group and Z is an oxygen atom or a sulfur atom.

13. A butenoic acid derivative of the formula:

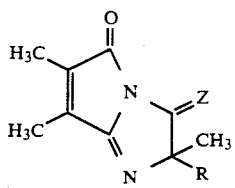   (I-d')

wherein R is an ethyl group, an isopropyl group or a cyclopropyl group and Z is an oxygen atom or a sulfur atom.

14. A butenoic acid derivative of the formula:

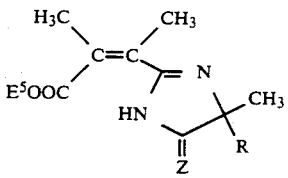   (I-e)

wherein R is an ethyl group, an isopropyl group or a cyclopropyl group, Z is an oxygen atom or a sulfur atom and $E^5$ is a salt-forming cation selected from the group consisting of ammonium, organic ammonium, alkali metals, alkaline earth metals, manganese (II), copper(ii), iron (II), iron (III), zinc (II), cobalt (II), lead (II), silver (I), aluminium (III) and nickel (II).

15. A butenoic acid derivative of the formula:

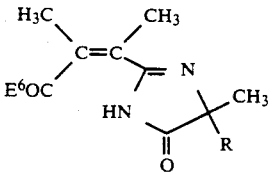   (I-f)

wherein R is an ethyl group, an isopropyl group or a cyclopropyl group and $E^6$ is either one of the following groups:

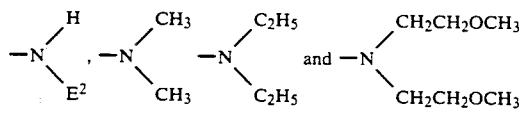

wherein $E^2$ is a hydrogen atom, a hydroxyl group, a $C_1$-$C_{12}$ alkyl group, a $C_3$-$C_6$ cycloalkyl group, a C₁-C₃ alkoxy-(C₁-C₁₂)alkyl group, a hydroxy(C₁-C₁₂)alkyl group, a cyano-(C₁-C₁₂)alkyl group, a C₃-C₁₂ alkenyl group, a C₃-C₁₂ alkynyl group, a carbamoyl(C₁-C₁₂)alkyl group, an aryl-(C₁-C₄)alkyl group, a C₁-C₃ alkoxycarbonyl(-C₁-C₁₂)alkyl group or a tetrahydrofurfuryl group.

16. A butenoic acid derivative of the formula:

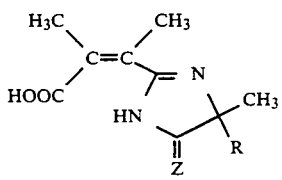
(I-g)

wherein R is an ethyl group, an isopropyl group or a cyclopropyl group and Z is an oxygen atom or a sulfur atom, or its salt.

17. A herbicidal composition which comprises a ideally effective amount of the butenoic acid derivative as claimed in claim 1, and an inert carrier or diluent.

18. A method for controlling or exterminating undesired weeds which comprises applying a herbicidally effective amount of the butenoic acid derivative as claimed in claim 1 to an area where weeds grow or will grow.

19. The method according to claim 18, wherein the area is a non-agricultural field.

20. A compound of the formula:

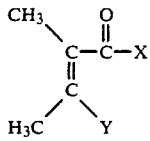

wherein X is hydroxy; a group of the formula: OE¹ wherein E¹ is C₁-C₈ alkyl, C₃-C₁₂ alkenyl, phenyl (C₁-C₁₂)alkyl optionally substituted with one or more C₁-C₁₂ alkyl groups on the benzene ring; a salt forming cation of alkali metals, ammonium, and alkaline earth metals; a group of the formula: —NH—E₂ wherein E₂ is H, OH, C₁-C₁₂ alkyl, C₃-C₁₂ alkenyl, or phenyl (C₁-C₄)alkyl;

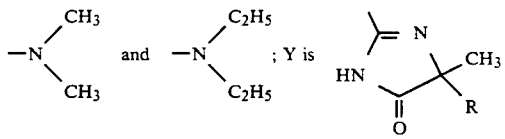

wherein R is ethyl, isopropyl, cyclopropyl, or their salt forms.

21. A compound of the formula:

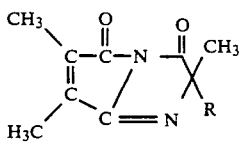

wherein R is an ethyl group, an isopropyl group, or a cyclopropyl group, or their salt forms.

22. A herbicidal composition comprising an effective herbicidal amount of the compound of claim 21, and an inert carrier or diluent.

23. A herbicidal composition comprising an effective herbicidal amount of the compound of claim 22, and an inert carrier or diluent.

24. A method for controlling or exterminating undesired weeds which comprises applying a herbicidally effective amount of the compound of claim 20 to the area where weeds grow or will grow.

25. A method for controlling or exterminating undesired weeds which comprises applying a herbicidally effective amount of the compound of claim 21 to the area where weeds grow or will grow.

* * * * *